US008357673B2

(12) United States Patent
Cankar et al.

(10) Patent No.: US 8,357,673 B2
(45) Date of Patent: Jan. 22, 2013

(54) 4-ARYLAZO-3,5-DIAMINO-PYRAZOLE COMPOUNDS AND USE THEREOF

(75) Inventors: Petr Cankar, Olomouc (CZ); Iveta Frysova, Mohelnice (CZ); Vladimir Krystof, Olomouc (CZ); Rene Lenobel, Sternberk (CZ); Jan Slouka, Olomouc (CZ); Miroslav Strnad, Olomouc (CZ); Peter Martin Fischer, Beeston (GB)

(73) Assignee: Univerzita Palackeho V Olomouci, Olomouc (CZ)

( * ) Notice: Subject to any disclaimer, the term of this patent is extended or adjusted under 35 U.S.C. 154(b) by 1057 days.

(21) Appl. No.: 11/661,003

(22) PCT Filed: Sep. 1, 2005

(86) PCT No.: PCT/GB2005/003383
§ 371 (c)(1),
(2), (4) Date: May 2, 2008

(87) PCT Pub. No.: WO2006/024858
PCT Pub. Date: Mar. 9, 2006

(65) Prior Publication Data
US 2008/0312238 A1 Dec. 18, 2008

(30) Foreign Application Priority Data
Sep. 1, 2004 (GB) .................................. 0419416.3

(51) Int. Cl.
A61K 31/655 (2006.01)
A61P 35/00 (2006.01)
A61P 35/02 (2006.01)
C07D 231/38 (2006.01)
C07D 403/12 (2006.01)

(52) U.S. Cl. ......... 514/150; 534/757; 534/759; 534/794
(58) Field of Classification Search ........................ None
See application file for complete search history.

(56) References Cited

U.S. PATENT DOCUMENTS

| | | | |
|---|---|---|---|
| 6,214,813 B1 * | 4/2001 | Zhang et al. ................... | 514/150 |
| 6,221,873 B1 | 4/2001 | Havlicek et al. | |
| 6,436,915 B1 * | 8/2002 | Zhang et al. ................... | 514/150 |
| 6,531,479 B2 | 3/2003 | Wang et al. | |
| 6,569,833 B1 | 5/2003 | Fahraeus | |
| 6,699,854 B2 | 3/2004 | Wang et al. | |
| 6,703,395 B2 | 3/2004 | Havlicek | |
| 7,041,701 B2 | 5/2006 | Hajduch et al. | |
| 7,105,503 B2 * | 9/2006 | Zhang et al. ................... | 514/150 |
| 7,875,728 B2 * | 1/2011 | Zhang et al. ................. | 548/371.4 |
| 2003/0060453 A1 * | 3/2003 | Zhang et al. ..................... | 514/94 |

FOREIGN PATENT DOCUMENTS

| | | |
|---|---|---|
| WO | WO-02/22601 A1 | 3/2002 |
| WO | WO-03/002565 A1 | 1/2003 |
| WO | WO-2004/018473 A2 | 3/2004 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al., Advanced Drug Delivery Reviews, 48 (2001), pp. 3-26.*
Radeva, Galina et al., "Overexpressiion of the Integrin-linked Kinase Promotes Anchorage-independent Cell Cycle Progression", Journal of Biological Chemistry, 272(21), 13937-13944, 1997.*
Golub et al., Science, 286, 531-537, 1999.*
El-Gaby, Mohamed S.A. et al., "Preparation of Some Novel 3,5-Diaminopyrazole, Pyrazolo-[1,5-a] {1,3,5}Triazine and Pyrazolo{1,5-a}-Pyrimidine Derivatives Containing Sulfonamido Moieties as Antimicrobial Agents," *Acta Chim. Slov.*, vol. 49:159-171 (2002).
Elgemeie, Galal H. et al., "Preparation and characterization of novel methylsulfanyl-pyrazolopyrimidine and methylsulfanyl-pyrazolotriazine azo dyes," *Pigment and Resin Technology*, vol. 31(5):297-309 (2002).
Fathy, N.M. et al., "Behaviour of 3,5-Diaminopyrazoles Towards Activated Double Bond Systems: Novel Synthesis of Pyrazolo [1,5-a] Pyrimidines," *Egypt. J. Pharma. Sci.*, vol. 33(1-2):1-9 (1992).
Shvekhgeimer, M.-G.A., Synthesis of Novel 3,5-Diamino-4-(2-Cyano-Arylazo)Pyrazoles, *Chemistry of Heterocyclic Compounds*, vol. 37(3):370-371 (2001).
Wiedermannová, Iveta et al., "Oxo Derivatives of Quinoxaline VI Synthesis of Some Arylhydrazones of 6,7-Disubstituted-1,2-Dihydro-Quinoxaline-3-Carbaldehyde," *Acta Universitatis Palackianae Olomucensis, Facultas Rerum Naturalium*, vol. 41:59-63 (2002).
Zhu, Youyu et al., "Study on the color reaction of palladium with 4-(6'-methylbenzothiazolyl-2'-azo)-3,5-diaminopyrazole and its application," *Huaxue Shiji*, vol. 15(5):274-276 (1993).
Written Opinion for Application No. PCT/GB2005/003383, dated Mar. 6, 2007.

* cited by examiner

*Primary Examiner* — Fiona T Powers
(74) *Attorney, Agent, or Firm* — Nelson Mullins Riley & Scarborough LLP; Cynthia L. Kanik

(57) ABSTRACT

A series of mono- and binuclear 4-arylazo-3,5-diamino-pyrazoles which are useful for inhibition of cyclin-dependent kinases (preferably CDK9). Hence they can be used as antimitotic-, pro-apoptotic and antiinflammatory drugs, in particular, in chemotherapy of cancer and asthma, therapy of psoriasis and parasitoses as those caused by fungi or protists, treatment of Alzheimer's disease or as antineurodegenerative drugs, or to suppress immunostimulation. These compounds are useful in a variety of utilities, including as intermediates in the preparation of flame-retardants, diagnostic reagents and therapeutics, including antivirals and immunosuppressors.

2 Claims, 3 Drawing Sheets

4-ARYLAZO-3,5-DIAMINO-PYRAZOLE COMPOUNDS AND USE THEREOF

RELATED APPLICATIONS

The present application is a 35 U.S.C. 371 national stage filing of International Application No. PCT/GB2005/003383, filed on 1 Sep. 2005, which claims priority to Great Britain Application No. 0419416.3, filed 1 Sep. 2004. The entire contents of each of these applications are hereby incorporated by reference herein.

The present invention relates to arylazo-3,5-diamino-pyrazole derivatives and their therapeutic activity. More specifically, but not exclusively, the invention relates to compounds that are capable of inhibiting one or more protein kinases.

BACKGROUND TO THE INVENTION

The cyclin-dependent kinases (CDKs) are a family of serine/threonin protein kinases that play a key role in the regulation of progression through the cell division cycle. Individual CDKs phosphorylate distinct substrates in different phases of the cell cycle and therefore are usually classified as either G1, S, or G2/M phase specific. Regulation of these kinases is tightly controlled at different levels including interactions with negative and positive partners, activation by (de)phosphorylation and subcellular localization. Cell cycle dysregulation, a hallmark of transformed cells is accompanied with altered CDK activity in many cancers, caused either by changed expression or activation of CDKs and their interacting proteins. In particular, CDK2 and 4 are promising pharmacological targets for novel anticancer agents.

During the past decade, many potent and selective inhibitors of CDKs have been developed in SAR drug discovery programs, in spite of a relevant degree of active site similarity across the realm of protein kinases. Generally, CDK inhibitors comprise structurally distinct flat heterocyclic molecules, entering the active site and competing with ATP, a feature usually demonstrated by enzyme kinetic assay and inhibitor-CDK2 co-crystal analysis. Anti-CDK drugs possess prominent inhibitory properties against tumor cells both in vitro and in vivo and some of them (e.g. flavopiridol and roscovitine) are already under evaluation in clinical trials as new generation anticancer chemotherapeutics.

Proliferative disorders such as cancer are recognised as diseases of the cell cycle. It has been found that in tumour cells, the mechanisms that normally function to restrain cell division are defective, whilst those that promote division become more active. Cell-cycle regulatory compounds are pivotal in the modulation of abnormal cellular proliferation as they provide ideal therapeutic targets for a range of proliferative disorders.

The present invention seeks to provide new therapeutic compounds. More specifically, the invention relates to compounds that have broad therapeutic applications in the treatment of a number of different diseases and/or that are capable of inhibiting one or more protein kinases. In particular, the invention seeks to provide compounds having improved selectivity and efficiency index, i.e. that are less toxic and more efficacious than analogues known heretofore.

STATEMENT OF INVENTION

Aspects of the invention are set forth below and in the accompanying claims. The preferred embodiments outlined under each of the various sub-headings are applicable to all aspects of the invention.

The present invention relates to 4-arylazo-3,5-diamino-pyrazole derivatives. The compounds of the invention are useful for the inhibition of cyclin-dependent kinases, and thus have applications as antimitotic and apoptotic drugs, particularly anticancer and/or antiviral drugs. The compounds of the invention also have applications as anti-fungal agents, for example, in the treatment of aspergillosis, penicilliosis, actinomycosis and the like.

A first aspect of the invention relates to compounds of formula I, or pharmaceutically acceptable salts or solvates thereof,

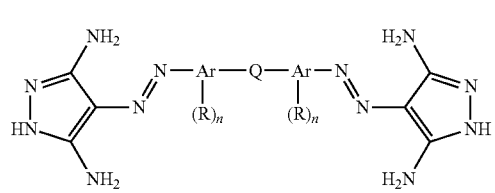

wherein
each Ar is independently a hydrocarbyl group comprising at least one fused or unfused aromatic ring;
each R is independently selected from:
  halogen, OH, hydroxylamino, $NH_2$, COOH, CN, $NO_2$, amido, sulfo, sulfamido and carbamoylamino;
  alkyl, cycloalkyl, arylalkyl, heteroalkyl, heteroarylalkyl, cycloalkyl alkyl and cycloheteroalkyl alkyl, each of which may be optionally substituted by one or more substituents selected from halogen, $NO_2$, OH, alkoxy, $NH_2$, COOH, $CONH_2$ and $CF_3$; and
Q is —N=N—, —C≡C—, —$(CH_2)_m$—, —CH=CH—, —O—, —C(O)—, —$SO_2$—, —NH—C(O)— or Ar′, where Ar′ is a fused or unfused aromatic group;
m and each n are each independently 0, 1, 2, 3, 4 or 5.

A second aspect of the invention relates to a pharmaceutical composition comprising a compound of formula I as defined above and a pharmaceutically acceptable diluent, excipient or carrier.

A third aspect of the invention relates to the use of a compound of formula I as defined above in the preparation of a medicament for treating a proliferative disorder.

A fourth aspect of the invention relates to a method of treating a proliferative disorder, said method comprising administering to a subject in need thereof, a compound of formula I as defined above.

A fifth aspect of the invention relates to the use of a compound of formula I as defined above in the preparation of a medicament for treating a viral disorder.

A sixth aspect of the invention relates to a method of treating a viral disorder, said method comprising administering to a subject in need thereof, a compound of formula I as defined above.

A seventh aspect of the invention relates to a method of inhibiting one or more of a cyclin dependent kinase, GSK, aurora kinase or a polo-like kinase in a cell, said method comprising contacting the cell with a compound of formula I as defined above.

An eighth aspect of the invention relates to a method of inhibiting cell proliferation and/or inducing apoptosis in a mammal, said method comprising contacting the cell with a compound of formula I as defined above.

A ninth aspect of the invention relates to the use of a compound of formula II, or a pharmaceutically acceptable salt or solvate thereof,

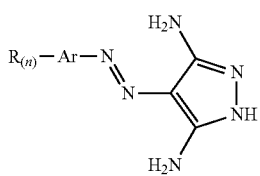

wherein
Ar is a hydrocarbyl group comprising at least one fused or unfused aromatic ring;
each R is independently selected from:
  halogen, OH, hydroxylamino, $NH_2$, COOH, CN, $NO_2$, amido, sulfo, sulfamido and carbamoylamino;
  alkyl, cycloalkyl, arylalkyl, heteroalkyl, heteroarylalkyl, cycloalkyl alkyl, cycloheteroalkyl alkyl, each of which may be optionally substituted by one or more substituents selected from halogen, $NO_2$, OH, alkoxy, $NH_2$, COOH, $CONH_2$ and $CF_3$; and
n is 0, 1, 2, 3, 4 or 5;
in the preparation of a medicament for treating a viral disorder.

A tenth aspect of the invention relates to the use of a compound of formula II as defined above in the preparation of a medicament for treating a CDK-dependent disorder, a GSK-dependent disorder, an aurora kinase-dependent disorder or a polo-like kinase-dependent disorder.

An eleventh aspect of the invention relates to a method of inhibiting one or more of a cyclin dependent kinase, GSK, aurora kinase or a polo-like kinase in a subject, said method comprising administering to the subject a compound of formula II as defined above, or a pharmaceutically acceptable salt thereof.

A twelfth aspect of the invention relates to selected compounds of formula II as set forth in the accompanying claims, and pharmaceutical compositions thereof.

DETAILED DESCRIPTION

As used herein, the term "hydrocarbyl" refers to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, phosphorus and silicon.

As used herein, and unless modified by the immediate context:

"Halogen" or "halo" preferably refers to fluorine, bromine, chlorine and iodine atoms.

"Hydroxy" refers to the group —OH.

"Mercapto" refers to the group —SH.

"Alkyl" preferably refers to branched or unbranched $C_1$-$C_8$ alkyl chain which is saturated or unsaturated. Thus, the term "alkyl" when used herein encompasses alkyl alkenyl and alkynyl groups. Alkenyl groups preferably have 2 to 8 carbon atoms, alkynyl groups preferably have 3 to 8 carbon atoms. Such groups as methyl, ethyl, propyl, isopropyl, n-butyl, isobutyl, tert-butyl, allyl, ethynyl, propargyl, and the like can exemplify this term.

"Substituted alkyl" preferably refers to alkyl as described above including one to six, in particular 1 to 3 substituents such as hydroxyl, mercapto, alkylthio, halogen, alkoxy, acyloxy, amino, acylamino, hydrazino, carbamoyl, amido, carboxyl, sulfo, acyl, guanidino and the like. These groups may be attached to any carbon atom of the alkyl moiety.

"Alkoxy" denotes the group —$OR^1$, where $R^1$ is alkyl, substituted alkyl, aryl, substituted aryl, arylalkyl, substituted arylalkyl, cycloalkyl, substituted cycloalkyl, cycloheteroalkyl or substituted cycloheteroalkyl as defined herein.

"Alkylthio" denotes the group —$SR^2$, where $R^2$ is as defined for $R^1$ above.

"Sulfo" denotes the group —$SO_3R^3$, where $R^3$ is H, alkyl or substituted alkyl as defined above.

"Sulfamido" denotes to the group $SO_2NR^4R^5$ where $R^4$ and $R^5$ are each independently H, alkyl or substituted alkyl as defined above.

"Acyl" denotes groups —$C(O)R^6$, where $R^6$ is alkyl, substituted alkyl, aryl, substituted aryl, arylalkyl, substituted arylalkyl, cycloalkyl, substituted cycloalkyl as defined herein.

"Aryloxy" denotes groups —$OAr^1$, where $Ar^1$ is an aryl, substituted aryl, heteroaryl or substituted heteroaryl group as defined herein.

"Alkylamino" denotes the group —$NR^7R^8$, where $R^7$ and $R^8$ are each independently hydrogen, alkyl, substituted alkyl, aryl, substituted aryl, heteroaryl or substituted heteroaryl as defined herein.

"Amido" denotes the group —$C(O)NR^9R^{10}$, where $R^9$ and $R^{10}$ are each independently hydrogen, alkyl, substituted alkyl, aryl, substituted aryl, heteroaryl, substituted heteroaryl as defined herein.

"Carboxyl" denotes the group —$C(O)OR^{11}$, where $R^{11}$ is hydrogen, alkyl, substituted alkyl, aryl, substituted aryl, heteroaryl or substituted heteroaryl as defined herein.

"Carbamino" denotes the group —$NHCOOR^{11}$, where $R^{11}$ is as defined above.

"Acylamino denotes the group —$NHCOR^{12}$, where $R^{12}$ may be alkyl, substituted alkyl, heterocycle, aryl, substituted aryl, heteroaryl and substituted heteroaryl as defined herein.

"Carbamoylamino" denotes the group —$NHCOOR^{13}$, where $R^{13}$ is alkyl or aryl.

"Aryl" or "Ar" refers to a hydrocarbyl group comprising at least one fused or unfused aromatic ring. Preferably, the aryl group has more than six, in particular 6 to 10 carbon atoms.

"Substituted aryl" refers to aryl as described above which is optionally substituted with one or more functional groups, in particular 1 to 5 substituents, such as halogen, alkyl, hydroxy, amino, acylamino, carbamoylamino, hydrazino, mercapto, alkoxy, alkylthio, alkylamino, amido, carboxyl, nitro, sulfo and the like as defined herein.

"Heterocycle" refers to a unsaturated or aromatic carbocyclic group preferably having 1 to 3 rings and having at least one, preferably 1 to 3 and in particular 1 or 2 heteroatoms, such as N, O or S, within the ring; the ring can be single (e.g. pyranyl, pyridyl or furyl) or multiple condensed (e.g., quinazolinyl, purinyl, quinolinyl or benzofuranyl) each of which may be optionally unsubstituted or substituted with one or more substituents selected from halogen, amino, hydroxy, cyano, nitro, mercapto, alkoxy, alkylamino, acylamino, carbamoylamino, acyloxy, dialkylamino, alkylthio carboxyl, amido, sulfo, sulfamido, and the like as defined above. The heterocycle group preferably has 5 to 10 ring atoms, which are either carbon atoms or heteroatoms as defined above.

"Heteroaryl" refers to a heterocycle in which at least one heterocyclic ring is aromatic.

"Substituted heteroaryl" refers to a heterocycle optionally mono or poly substituted with one or more functional groups, in particular 1 to 3 substituents selected from halogen, amino, hydroxy, cyano, nitro, mercapto, alkoxy, alkylamino, acylamino, carbamoylamino, acyloxy, dialkylamino, alkylthio carboxyl, amido, sulfo, sulfamido, and the like.

"Arylalkyl" refers to the group —$R^{14}$—Ar where Ar is an aryl group and $R^{14}$ is alkyl or substituted alkyl group as defined above. The aryl groups can optionally be unsubstituted or substituted as defined above with one or more substituents selected from halogen, amino, acylamino, carbamoylamino, hydrazino, acyloxy, alkyl, hydroxyl, alkoxy, alkylthio, alkylamino, amido, carboxyl, hydroxy, aryl, nitro, mercapto, sulfo and the like.

"Heteroalkyl" refers to the an alkyl group as defined above wherein one or more carbons are replaced by a heteroatom, for example where one or more carbons are replaced by NH, O or S. Heteroalkyl groups can optionally be unsubstituted or substituted as defined above with one or more substituents selected from halogen, amino, hydroxy, cyano, nitro, mercapto, alkoxy, alkylamino, acylamino, carbamoylamino, acyloxy, dialkylamino, alkylthio, carboxyl, amido, sulfo, sulfamido, and the like.

"Heteroarylalkyl" refers to the group —$R^{16}$-HetAr where HetAr is an heteroaryl group and $R^{16}$ is alkyl or substituted alkyl as defined above. Heteroarylalkyl groups can optionally be unsubstituted or substituted as defined above with one or more substituents selected from halogen, alkyl, substituted alkyl, alkoxy, alkylthio, nitro, mercapto, sulfo and the like.

"Cycloalkyl" refers to a cyclic or polycyclic alkyl group preferably containing 3 to 15 carbon atoms. Preferably, the cycloalkyl is divalent.

"Substituted cycloalkyl" refers to a cycloalkyl group comprising one or more substituents as defined above with one or more substituents selected from halogen, amino, hydroxy, cyano, nitro, mercapto, alkoxy, alkylamino, acylamino, carbamoylamino, acyloxy, dialkylamino, alkylthio, carboxyl, amido, sulfo, sulfamido, and the like.

"Cycloheteroalkyl" refers to a cycloalkyl group as defined above wherein one or more, preferably 1 to 3, of the ring methylene groups are replaced with a heteroatom (e.g., NH, O, S)

"Substituted cycloheteroalkyl" refers to a cycloheteroalkyl group as herein defined which contains one or more substituents as defined above, such as halogen, amino, hydroxy, cyano, nitro, mercapto, alkoxy, alkylamino, acylamino, carbamoylamino, acyloxy, dialkylamino, alkylthio, carboxyl, amido, sulfo, sulfamido and the like.

"Cycloalkyl alkyl" denotes the group —$R^{17}$-cycloalkyl where cycloalkyl is a cycloalkyl group as defined above and $R^{17}$ is an alkyl or substituted alkyl as defined above. Cycloalkyl groups can optionally be unsubstituted or substituted as defined above with one or more substituents selected from halogen, amino, hydroxy, cyano, nitro, mercapto, alkoxy, alkylamino, acylamino, carbamoylamino, acyloxy, dialkylamino, alkylthio, carboxyl, amido, sulfo, sulfamido and the like.

"Cycloheteroalkyl alkyl" denotes the group —$R^{18}$-cycloheteroalkyl where $R^{18}$ is a alkyl or substituted alkyl as defined above and cycloheteroalkyl as as defined above. Cycloheteroalkyl alkyl groups can optionally be unsubstituted or substituted as defined above with one or more substituents selected from halogen, amino, hydroxy, cyano, nitro, mercapto, alkoxy, alkylamino, acylamino, carbamoylamino, acyloxy, dialkylamino, alkylthio, carboxyl, amido, sulfo, sulfamido, and the like.

Compounds of Formula I

As mentioned above, a first aspect of the invention relates to compounds of formula I as defined above.

In one preferred embodiment, each Ar is independently aryl, bis-aryl, heteroaryl, bis-heteroaryl, arylalkyl, heteroarylalkyl or a fused multiple ring system in which at least one ring is aromatic.

In another preferred embodiment, each Ar is independently selected from phenyl, biphenyl, 1-naphthyl, 2-naphthyl, o-, m-, and p-phenylene, 1,2-, 1,3-, 1,4-, 1,5-, 1,6-, 1,7-, 1,8-, 2,6-, and 2,7-naphthalen-diyl, 1,2,3,4-tetrahydronaphthyl, fluorenyl, pyrazolyl, thiazolyl, thienyl, pyridyl, quinolyl, indenyl, anthryl, and phenanthrenyl, each of which may be optionally substituted with one or more substituents selected from halogen, hydroxy, alkoxy, amino, hydrazo, mercapto, carboxyl, cyano, nitro, amido, sulfo, sulfamido, acylamino, acyloxy, alkylamino, dialkylamino, alkylthio and carbamoyl.

In one preferred embodiment, Ar is a group of formula $R_a$-HetAr$^a$, wherein:
  $R_a$ is a $C_1$-$C_6$ alkylene, alkenylene or alkynylene group, each of which may be optionally substituted with one or more substituents selected from halogen, hydroxy, alkoxy and cyano; and
  HetAr$^a$ is selected from benzothienyl, naphthothienyl, benzofuranyl, chromenyl, indolyl, isoindolyl, indazolyl, quinolyl, isoquinolyl, phthalazinyl, quinoxalinyl, cinnolinyl, quinazolinyl, each of which may be optionally substituted with one or more substituents selected from halogen, hydroxy, alkoxy, amino, hydrazo, mercapto, carboxyl, cyano, nitro, amido, sulfo, sulfamido, acylamino, acyloxy, alkylamino, dialkylamino, alkylthio and carbamoyl.

In another preferred embodiment, Ar is a group of formula $R_b$Ar$^b$, wherein
  $R_b$ is a $C_1$-$C_6$ alkylene, alkenylene or alkynylene group each of which may be optionally substituted by one or more substituents selected from halogen, hydroxy, alkoxy and cyano; and
  Ar$^b$ is selected from phenyl, biphenyl, 1-naphthyl, 2-naphthyl, o-, m-, and p-phenylene, 1,2-, 1,3-, 1,4-, 1,5-, 1,6-, 1,7-, 1,8-, 2,6-, and 2,7-naphthalen diyl, tetrahydronaphthyl, fluorenyl, pyrazolyl, thiazolyl, thienyl, pyridyl, quinolyl, indenyl and phenanthrenyl, each of which may be optionally substituted by one or more substituents selected from halogen, hydroxy, alkoxy, amino, hydrazo, mercapto, carboxyl, cyano, nitro, amido, sulfo, sulfamido, acylamino, acyloxy, alkylamino, dialkylamino, alkylthio and carbamoyl.

Preferably, $R_a$ and $R_b$ are each independently selected from methylene, butan-1,2-diyl, butan-1,3-diyl, butan-1,4-diyl, pentamethylene, hexamethylene, ethylendiyl, allyl-1,3-diyl, methylethan-1,1-diyl, methylethan-1,2-diyl and butan-1,3-diyl.

In one preferred embodiment, R is a cycloheteroalkyl group selected from piperidinyl, piperazinyl, morpholinyl, pyrrolidinyl and imidazolidinyl, each of which may be optionally substituted with one or more substituents selected from halogen, hydroxy, alkoxy, amino, hydrazo, mercapto, carboxyl, cyano, nitro, amido, sulfo, sulfamido, acylamino, acyloxy, alkylamino, dialkylamino, alkylthio and carbamoyl.

In another preferred embodiment, R is a group of formula $R_c$(cycloheteroalkyl), wherein $R_c$ is $C_1$-$C_6$ alkylene, alkenylene or alkynylene, each of which may be optionally substituted with one or more substituents selected from halogen, hydroxy, alkoxy and cyano; and cycloheteroalkyl is as defined above.

In one preferred embodiment, Q is —N=N—, —C≡C—, a direct bond, —CH$_2$—, —CH$_2$CH$_2$—, CH=CH—, —O—, —C(O)—, —SO$_2$—, —NH—C(O)—, phenyl, biphenyl, or naphthyl.

In a more preferred embodiment, Q is a direct bond, CO, —CH$_2$—, —CH$_2$CH$_2$—, CH=CH—, —SO$_2$—, biphenyl, phenyl or naphthyl.

In another preferred embodiment, Q is a direct bond, CO, —CH$_2$—, CH=CH—, —SO$_2$—, phenyl or naphthyl.

In another preferred embodiment, Q is a direct bond, CO, —CH$_2$—, —CH$_2$CH$_2$—, CH=CH— or —SO$_2$—.

In one preferred embodiment, Ar' is 3,3'-biphenyl, 4,4'-biphenyl, 2-phenyl, 3-phenyl, 4-phenyl, 4-naphthyl, 5-naphthyl or 8-naphthyl.

In one preferred embodiment, Ar' is 2-phenyl, 3-phenyl, 4-phenyl, 4-naphthyl, 5-naphthyl or 8-naphthyl.

In one preferred embodiment, Ar is phenyl and Q is a direct bond. Thus, in one particularly preferred embodiment, —Ar(R)$_n$-Q-Ar(R)$_n$— is 3,3'-biphenyl or 4,4'-biphenyl.

In one preferred embodiment, Ar is independently selected from phenyl, benzyl, thiazolyl, naphthyl, pyrimidinyl, pyridinyl, quinolinyl, quinoxalinyl, 1,2-dihydroquinoxalin-2-one, and pyridazinyl, each of which may be optionally substituted by one or more substituents selected from halogen, OH, NO$_2$, NH$_2$, CF$_3$, alkyl, substituted alkyl, alkoxy, substituted alkoxy alkylthio and sulfonyl.

In another preferred embodiment, each Ar is independently selected from phenyl, benzyl, thiazol-2-yl, naphth-1-yl, naphth-2-yl, pyrimidin-2-yl, pyrimidin-3-yl, pyridin-3-yl, pyridin-2-yl, quinolin-5-yl, quinolin-8-yl, 1,2-dihydroquinoxalin-2-one and pyridazin-3-yl, each of which may be optionally substituted by one or more substituents selected from halogen, OH, NO$_2$, NH$_2$, CF$_3$, alkyl, substituted alkyl, alkoxy, substituted alkoxy alkylthio and sulfonyl.

In another preferred embodiment, each Ar is independently selected from phenyl, benzyl, thiazol-2-yl, naphth-1-yl, naphth-2-yl, pyrimidin-2-yl, pyrimidin-3-yl, pyridin-3-yl, pyridin-2-yl, quinolin-5-yl, quinolin-8-yl, 1,2-dihydroquinoxalin-2-one and pyridazin-3-yl, each of which may be optionally substituted by one or more substituents selected from halogen, OH, NO$_2$, NH$_2$, CF$_3$, methyl, methoxy, tetrafluoromethoxy, tetrafluoroethoxy, MeS and sulfonyl.

In one especially preferred embodiment of the invention, each Ar is independently a phenyl group, more preferably a 3-phenyl or 4-phenyl group, optionally substituted by one or more substituents selected from halogen, OH, NO$_2$, NH$_2$, CF$_3$, methyl, methoxy, tetrafluoromethoxy, tetrafluoroethoxy, MeS and sulfonyl.

In one particularly preferred embodiment, the Ar groups are the same.

In one especially preferred embodiment of the invention, Ar is 2-phenyl, 3-phenyl or 4-phenyl, more preferably 3-phenyl or 4-phenyl.

In one especially preferred embodiment of the invention, each Ar is 3,5-dioxo-2,3,4,5-tetrahydro-[1,2,4]triazin-6-yl.

In another especially preferred embodiment of the invention, each Ar is 6-carboxy-3,5-dioxo-2,3,4,5-tetrahydro-[1,2,4]triazin-2-yl.

In one preferred embodiment, n is zero.

In a more preferred embodiment, Ar is phenyl and n is zero.

More preferably, Ar is 2-phenyl, 3-phenyl or 4-phenyl, more preferably 3-phenyl or 4-phenyl and n is zero.

In one especially preferred embodiment, the compound of formula I is selected from the following:

1,3-bis-(3,5-dioxo-2,3,4,5-tetrahydro-[1,2,4]triazin-6-yl)-2-[(3,5-diamino-pyrazol-4-yl)-azo]-benzene;
1,3-bis-(6-carboxy-3,5-dioxo-2,3,4,5-tetrahydro-[1,2,4]triazin-2-yl)-5-[(3,5-diamino-pyrazol-4-yl)-azo]-benzene;
4,4'-bis-[(3,5-diamino-pyrazol-4-yl)-azo]-biphenyl;
3,3'-bis-[(3,5-diamino-pyrazol-4-yl)-azo]-biphenyl;
3,3'-bis-[(3,5-diamino-pyrazol-4-yl)-azo]-biphenyl;
1,1-bis-{4-[(3,5-diamino-pyrazol-4-yl)-azo]-phenyl}-methane;
1,1-bis-{3-[(3,5-diamino-pyrazol-4-yl)-azo]-phenyl}-methane;
1,1-bis-{4-[(3,5-diamino-pyrazol-4-yl)-azo]-phenyl}-methanone;
1,1-bis-{3-[(3,5-diamino-pyrazol-4-yl)-azo]-phenyl}-methanone;
1,1-bis-{4-[(3,5-diamino-pyrazol-4-yl)-azo]-phenyl}-sulfone;
1,1-bis-{3-[(3,5-diamino-pyrazol-4-yl)-azo]-phenyl}-sulfone;
1,2-bis-{4-[(3,5-diamino-pyrazol-4-yl)-azo]-phenyl}-ethene;
1,2-bis-{3-[(3,5-diamino-pyrazol-4-yl)-azo]-phenyl}-ethene;
1,3-bis-{3-[(3,5-diamino-pyrazol-4-yl)-azo]-phenyl}-benzene;
1,4-bis-{3-[(3,5-diamino-pyrazol-4-yl)-azo]-phenyl}-benzene;
1,4-bis-{3-[(3,5-diamino-pyrazol-4-yl)-azo]-phenyl}-naphthalene;
1,5-bis-{3-[(3,5-diamino-pyrazol-4-yl)-azo]-phenyl}-naphthalene;
1,8-bis-{3-[(3,5-diamino-pyrazol-4-yl)-azo]-phenyl}-naphthalene;
and pharmaceutically acceptable salts and solvates thereof.

Compounds of Formula II

Another aspect of the invention relates to the use of a compound of formula II as defined above, or a pharmaceutically acceptable salt thereof, in the preparation of medicament for treating a viral disorder.

Another aspect of the invention relates to the use of a compound of formula II as defined above in the preparation of a medicament for treating a CDK-dependent disorder, a GSK-dependent disorder, an aurora kinase-dependent disorder or a polo-like kinase-dependent disorder.

Another aspect of the invention relates to a method of inhibiting one or more of a cyclin dependent kinase, GSK, aurora kinase or a polo-like kinase in a subject, said method comprising administering to the subject a compound of formula II as defined above, or a pharmaceutically acceptable salt thereof.

For compounds of formula II, preferred embodiments for Ar, R and n are as defined above for compounds of formula I.

In one particularly preferred embodiment, for compounds of formula II, Ar is phenyl optionally substituted by one or more substituents selected from OH, NO$_2$, alkoxy, carboxy, halo, haloalkyl, haloalkoxy, amino, hydroxyalkyl, alkyl and thioalkyl.

In a more preferred embodiment, for compounds of formula II, Ar is phenyl optionally substituted by one or more substituents selected from OH, NO$_2$, MeO, carboxy, Cl, Br, I, CF$_3$, CF$_3$O, amino, CH$_2$OH, CF$_2$HCF$_2$O, Me and SMe.

Preferably, for treating one or more of a viral disorder, a CDK-dependent disorder, a GSK-dependent disorder, an aurora kinase-dependent disorder or a polo-like kinase-dependent disorder, the compound of formula II is selected from the following:

3,5-diamino-4-(2-hydroxy)phenylazo-pyrazole;
3,5-diamino-4-(3-hydroxy)phenylazo-pyrazole;
3,5-diamino-4-(4-hydroxy)phenylazo-pyrazole;
3,5-diamino-4-(2-nitro)phenylazo-pyrazole;
3,5-diamino-4-(3-nitro)phenylazo-pyrazole;
3,5-diamino-4-(4-nitro)phenylazo-pyrazole;
3,5-diamino-4-(2-chloro)phenylazo-pyrazole;
3,5-diamino-4-(3-chloro)phenylazo-pyrazole;

3,5-diamino-4-(4-chloro)phenylazo-pyrazole;
3,5-diamino-4-(2-bromo)phenylazo-pyrazole;
3,5-diamino-4-(3-bromo)phenylazo-pyrazole;
3,5-diamino-4-(4-bromo)phenylazo-pyrazole;
3,5-diamino-4-(2,3-bis(trifluoromethyl))phenylazo-pyrazole;
3,5-diamino-4-(2,4-bis(trifluoromethyl))phenylazo-pyrazole;
3,5-diamino-4-(2,5-bis(trifluoromethyl))phenylazo-pyrazole;
3,5-diamino-4-(3,5-bis(trifluoromethyl))phenylazo-pyrazole;
3,5-diamino-4-(4-bromo-3-chloro)phenylazo-pyrazole;
3,5-diamino-4-(4-bromo-2-chloro)phenylazo-pyrazole;
3,5-diamino-4-(2-bromo-5,6-difluoro)phenylazo-pyrazole;
3,5-diamino-4-(2-bromo-4,6-difluoro)phenylazo-pyrazole;
3,5-diamino-4-(2-bromo-6-chloro-4-(trifluoromethyl))phenylazo-pyrazole;
3,5-diamino-4-(4-bromo-2,6-difluoro)phenylazo-pyrazole;
3,5-diamino-4-(4-bromo-2-fluoro)phenylazo-pyrazole;
3,5-diamino-4-(2-bromo-4-fluoro)phenylazo-pyrazole;
3,5-diamino-4-(2-bromo-4-methyl)phenylazo-pyrazole;
3,5-diamino-4-(3-bromo-2-methyl)phenylazo-pyrazole;
3,5-diamino-4-(4-bromo-3-methyl)phenylazo-pyrazole;
3,5-diamino-4-(2-bromo-4-(trifluoromethoxy)phenylazo-pyrazole;
3,5-diamino-4-(3-bromo-4-(trifluoromethoxy)phenylazo-pyrazole;
3,5-diamino-4-(4-bromo-2-(trifluoromethoxy)phenylazo-pyrazole;
3,5-diamino-4-(2-bromo-4,5,6-trifluoro)phenylazo-pyrazole;
3,5-diamino-4-(2,4-dibromo)phenylazo-pyrazole;
3,5-diamino-4-(2,5-dibromo)phenylazo-pyrazole;
3,5-diamino-4-(2,4-dibromo-3,6-dichloro)phenylazo-pyrazole;
3,5-diamino-4-(2,6-dibromo-4-fluoro)phenylazo-pyrazole;
3,5-diamino-4-(2,6-dibromo-4-(trifluoromethoxy))phenylazo-pyrazole;
3,5-diamino-4-(2,4-dibromo-6-(trifluoromethoxy))phenylazo-pyrazole;
3,5-diamino-4-(2,6-dibromo-4-(trifluoromethyl))phenylazo-pyrazole;
3,5-diamino-4-(2,3-dichloro)phenylazo-pyrazole;
3,5-diamino-4-(2,4-dichloro)phenylazo-pyrazole;
3,5-diamino-4-(2,5-dichloro)phenylazo-pyrazole;
3,5-diamino-4-(2,6-dichloro)phenylazo-pyrazole;
3,5-diamino-4-(3,4-dichloro)phenylazo-pyrazole;
3,5-diamino-4-(3,5-dichloro)phenylazo-pyrazole;
3,5-diamino-4-(2,6-dichloro-4-(trifluoromethoxy))phenylazo-pyrazole;
3,5-diamino-4-(2,4-dichloro-6-(trifluoromethoxy))phenylazo-pyrazole;
3,5-diamino-4-(2,6-dichloro-4-(trifluoromethyl))phenylazo-pyrazole;
3,5-diamino-4-(2,3-difluoro)phenylazo-pyrazole;
3,5-diamino-4-(2,4-difluoro)phenylazo-pyrazole;
3,5-diamino-4-(2,5-difluoro)phenylazo-pyrazole;
3,5-diamino-4-(2,6-difluoro)phenylazo-pyrazole;
3,5-diamino-4-(3,4-difluoro)phenylazo-pyrazole;
3,5-diamino-4-(3,5-difluoro)phenylazo-pyrazole;
3,5-diamino-4-(2-difluoromethoxy)phenylazo-pyrazole;
3,5-diamino-4-(2-difluoromethoxy-5-nitro)phenylazo-pyrazole;
3,5-diamino-4-(2,3-difluoro-6-nitro)phenylazo-pyrazole;
3,5-diamino-4-(2,4-diiodo)phenylazo-pyrazole;
3,5-diamino-4-(2,3-dimethyl)phenylazo-pyrazole;
3,5-diamino-4-(2,4-dimethyl)phenylazo-pyrazole;
3,5-diamino-4-(2,3-dimethyl-6-nitro)phenylazo-pyrazole;
3,5-diamino-4-(2,3-dimethoxy)phenylazo-pyrazole;
3,5-diamino-4-(2,4-dimethoxy)phenylazo-pyrazole;
3,5-diamino-4-(2,3-dinitro-6-methyl)phenylazo-pyrazole;
3,5-diamino-4-(4-hydroxy-2-methyl)phenylazo-pyrazole;
3,5-diamino-4-(3-chloro-2,6-dibromo-4-fluoro)phenylazo-pyrazole;
3,5-diamino-4-(2-chloro-4-fluoro)phenylazo-pyrazole;
3,5-diamino-4-(2-chloro-5-fluoro)phenylazo-pyrazole;
3,5-diamino-4-(2-chloro-6-fluoro)phenylazo-pyrazole;
3,5-diamino-4-(3-chloro-2-fluoro)phenylazo-pyrazole;
3,5-diamino-4-(3-chloro-4-fluoro)phenylazo-pyrazole;
3,5-diamino-4-(4-chloro-2-fluoro)phenylazo-pyrazole;
3,5-diamino-4-(5-chloro-2-fluoro)phenylazo-pyrazole;
3,5-diamino-4-(3-chloro-4-fluoro)phenylazo-pyrazole;
3,5-diamino-4-(2-chloro-4-fluoro-5-methyl)phenylazo-pyrazole;
3,5-diamino-4-(5-chloro-4-fluoro-2-nitro)phenylazo-pyrazole;
3,5-diamino-4-(5-chloro-2-hydroxy)phenylazo-pyrazole;
3,5-diamino-4-(4-chloro-2-iodo)phenylazo-pyrazole;
3,5-diamino-4-(2-chloro-4-iodo)phenylazo-pyrazole;
3,5-diamino-4-(2-chloro-3-methyl)phenylazo-pyrazole;
3,5-diamino-4-(2-chloro-2-methyl)phenylazo-pyrazole;
3,5-diamino-4-(3-chloro-2-methyl)phenylazo-pyrazole;
3,5-diamino-4-(3-chloro-4-(trifluoromethoxy))phenylazo-pyrazole;
3,5-diamino-4-(4-chloro-2-(trifluoromethoxy))phenylazo-pyrazole;
3,5-diamino-4-(2-fluoro-4-iodo)phenylazo-pyrazole;
3,5-diamino-4-(2-fluoro-4-methyl)phenylazo-pyrazole;
3,5-diamino-4-(3-fluoro-2-methyl)phenylazo-pyrazole;
3,5-diamino-4-(2-fluoro-5-nitro)phenylazo-pyrazole;
3,5-diamino-4-(3-fluoro-4-methyl)phenylazo-pyrazole;
3,5-diamino-4-(4-fluoro-2-methyl)phenylazo-pyrazole;
3,5-diamino-4-(4-fluoro-3-methyl)phenylazo-pyrazole;
3,5-diamino-4-(5-fluoro-2-methyl)phenylazo-pyrazole;
3,5-diamino-4-(4-fluoro-2-nitro)phenylazo-pyrazole;
3,5-diamino-4-(4-fluoro-3-nitro)phenylazo-pyrazole;
3,5-diamino-4-(2-fluoro-4-(trifluoromethyl))phenylazo-pyrazole;
3,5-diamino-4-(2-iodo)phenylazo-pyrazole;
3,5-diamino-4-(3-iodo)phenylazo-pyrazole;
3,5-diamino-4-(4-iodo)phenylazo-pyrazole;
3,5-diamino-4-(2-methoxy)phenylazo-pyrazole;
3,5-diamino-4-(3-methoxy)phenylazo-pyrazole;
3,5-diamino-4-(4-methoxy)phenylazo-pyrazole;
3,5-diamino-4-(2-methoxy-5-methyl)phenylazo-pyrazole;
3,5-diamino-4-(2-methoxy-6-methyl)phenylazo-pyrazole;
3,5-diamino-4-(4-methoxy-2-methyl)phenylazo-pyrazole;
3,5-diamino-4-(4-methoxy-3-(trifluoromethyl))phenylazo-pyrazole;
3,5-diamino-4-(3-methoxy-4-(trifluoromethyl)phenylazo-pyrazole;
3,5-diamino-4-(2-methyl)phenylazo-pyrazole;
3,5-diamino-4-(3-methyl)phenylazo-pyrazole;
3,5-diamino-4-(4-methyl)phenylazo-pyrazole;
3,5-diamino-4-(2-methyl-3-(trifluoromethoxy))phenylazo-pyrazole;
3,5-diamino-4-(2-methyl-4-(trifluoromethoxy))phenylazo-pyrazole;
3,5-diamino-4-(2-methylthio)phenylazo-pyrazole;
3,5-diamino-4-(4-methylthio)phenylazo-pyrazole;
3,5-diamino-4-(2-nitro-4,5,6-trifluoro)phenylazo-pyrazole;
3,5-diamino-4-(2-nitro-4-(trifluoromethoxy))phenylazo-pyrazole;
3,5-diamino-4-(2-nitrotetrafluoro)phenylazo-pyrazole;

3,5-diamino-4-(2,3,4,5,6-pentabromo)phenylazo-pyrazole;
3,5-diamino-4-(2,3,4,5,6-pentafluoro)phenylazo-pyrazole;
3,5-diamino-4-(2,3,4,5-tetrachloro)phenylazo-pyrazole;
3,5-diamino-4-(2,3,5,6-tetrachloro)phenylazo-pyrazole;
3,5-diamino-4-(4-(1,1,2,2-tetrafluoroethoxy))phenylazo-pyrazole;
3,5-diamino-4-(2,3,4,5-tetrafluoro)phenylazo-pyrazole;
3,5-diamino-4-(2,3,4,6-tetrafluoro)phenylazo-pyrazole;
3,5-diamino-4-(2,3,5,6-tetrafluoro-4-(trifluoromethyl))phenylazo-pyrazole;
3,5-diamino-4-(2,4,6-tribromo)phenylazo-pyrazole;
3,5-diamino-4-(2,4,6-tribromo-3,5-diiodo)phenylazo-pyrazole;
3,5-diamino-4-(2,3,4-trichloro)phenylazo-pyrazole;
3,5-diamino-4-(2,4,5-trichloro)phenylazo-pyrazole;
3,5-diamino-4-(2,4,6-trichloro)phenylazo-pyrazole;
3,5-diamino-4-(2,4,5-trifluoro)phenylazo-pyrazole;
3,5-diamino-4-(2,3,5-trifluoro)phenylazo-pyrazole;
3,5-diamino-4-(2,3,6-trifluoro)phenylazo-pyrazole;
3,5-diamino-4-(2,3,4-trifluoro)phenylazo-pyrazole;
3,5-diamino-4-(2-trifluoromethoxy)phenylazo-pyrazole;
3,5-diamino-4-(3-trifluoromethoxy)phenylazo-pyrazole;
3,5-diamino-4-(4-trifluoromethoxy)phenylazo-pyrazole;
3,5-diamino-4-(2,3,4-trifluoro-6-nitro)phenylazo-pyrazole;
3,5-diamino-4-(2,4,5-trimethyl)phenylazo-pyrazole;
3,5-diamino-4-(2,4,6-trimethyl)phenylazo-pyrazole;
3,5-diamino-4-(3-trimethyl)phenylazo-pyrazole;
3,5-diamino-4-(3-trichloro-5-amino)phenylazo-pyrazole;
3,5-diamino-4-(3-trichloro-4-carboxy)phenylazo-pyrazole;
3,5-diamino-4-(3-amino-4-chloro)phenylazo-pyrazole;
3,5-diamino-4-(3-chloro-4-amino)phenylazo-pyrazole;
3,5-diamino-4-(3-carboxy-4-hydroxy)phenylazo-pyrazole;
3,5-diamino-4-(naphth-1-yl)phenylazo-pyrazole;
3,5-diamino-4-(5,6,7,8-tetrahydronaphthalene-1-yl)phenylazo-pyrazole;
N-({4-[(3,5-diamino-pyrazol-4-yl)azo]phenyl}sulfonyl)-acetamide;
N-[amino(imino)methyl]-4-[(3,5-diamino-pyrazol-4-yl)azo]-benzansulfonamide;
4-[(3,5-diaminopyrazol-4-yl)azo]-N-(thiazol-2-yl)-benzensulfonamide;
4-[(3,5-diamino-pyrazol-4-yl)-azo]-N-(4,6-dimethylpyrimidin-2-yl)benzensulfonamide;
4-[(3,5-diamino-pyrazol-4-yl)-azo]-N-(5-methoxypyrimidin-2-yl)-benzensulfonamide;
4-[(3,5-diamino-pyrazol-4-yl)-azo]-N-(6-methoxypyridazin-3-yl)-benzensulfonamide;
3-{2-[(3,5-diamino-pyrazol-4-yl)-azo]-phenyl}-1,2-dihydroquinoxaline-2-one;
3-{4-[(3,5-diamino-pyrazol-4-yl)-azo]-phenyl}-1,2-dihydro-quinoxaline-2-one;
3-{2-[(3,5-diamino-pyrazol-4-yl)-azo]benzyl}-1,2-dihydro-quinoxaline-2-one;
3-{4-[(3,5-Diaminopyrazol-4-yl)-azo]-benzyl}-1,2-dihydro-quinoxaline-2-one;
3-{2-[(3,5-diamino-pyrazol-4-yl)-azo]-phenyl}-1,2-dihydro-5,6-dimethylquinoxaline-2-one;
3-{2-[(3,5-diamino-pyrazol-4-yl)-azo]-phenyl}-1,2-dihydro-5,6-dichloro-quinoxaline-2-one;
3-{4-3,5-diamino-pyrazol-4-yl)-azo]-phenyl}-1,2-dihydro-5,6-dimethyl-quinoxaline-2-one;
3-{4-[(3,5-diamino-pyrazol-4-yl)-azo]-phenyl}-1,2-dihydro-5,6-dichloro-quinoxaline-2-one;
3-{2-[(3,5-Diamino-pyrazol-4-azo]benzyl}-1,2-dihydro-5,6-dimethyl-quinoxaline-2-one;
3-{2-[(3,5-Diamino-pyrazol-4-yl)-azo]-benzyl}-1,2-dihydro-5,6-dichloroquinoxaline-2-one;
3-{4-[(3,5-Diamino-pyrazol-4-yl)-azo]benzyl}-1,2-dihydro-5,6-dimethyl-quinoxaline-2-one;
3-{4-[(3,5-Diamino-pyrazol-4-yl)-azo]benzyl}-1,2-dihydro-5,6-dichloro-quinoxaline-2-one;
3-{3-(3,5-Dioxo-2,3,4,5-tetrahydro-[1,2,4]triazin-6-yl)-2-[(3,5-diaminopyrazol-4-yl)-azo]-phenyl}-1,2-dihydro-quinoxaline-2-one;
1,3-bis-(3,5-dioxo-2,3,4,5-tetrahydro-[1,2,4]triazin-6-yl)-2-[(3,5-diamino-pyrazol-4-yl)-azo]-benzene;
1,3-bis-(6-carboxy-3,5-dioxo-2,3,4,5-tetrahydro-[1,2,4]triazin-2-yl)-5-[(3,5-diamino-pyrazol-4-yl)-azo]-benzene;
7-[(3,5-Diamino-pyrazol-4-yl)-azo]-1,2-dihydro-quinoxaline-2-one;
4-[(pyridin-3-yl)-azo]-3,5-diamino-pyrazole;
4-[(quinoline-5-yl)-azo]-3,5-diamino-pyrazole;
4-[(quinoline-8-yl)-azo]-3,5-diamino-pyrazole;
3,5-diamino-4-(4-fluoro)phenylazo-pyrazole;
3,5-diamino-4-(phenyl)azo-pyrazole;
3,5-diamino-4-(2-carboxy)phenylazo-pyrazole;
3,5-diamino-4-(3-carboxy)phenylazo-pyrazole;
3,5-diamino-4-(4-carboxy)phenylazo-pyrazole;
3,5-diamino-4-(2-hydroxymethyl)phenylazo-pyrazole;
3,5-diamino-4-(4-aminomethyl)phenylazo-pyrazole;
3,5-diamino-4-(naphth-1-yl)azo-pyrazole; and
3,5-diamino-4-(naphth-2-yl)azo-pyrazole;
and pharmaceutically acceptable salts and solvates thereof.

More preferably, the compound of formula II is selected from the following:
3,5-diamino-4-(phenyl)azo-pyrazole;
3,5-diamino-4-(2-nitro)phenylazo-pyrazole;
3,5-diamino-4-(3-nitro)phenylazo-pyrazole;
3,5-diamino-4-(4-nitro)phenylazo-pyrazole;
3,5-diamino-4-(2-hydroxy)phenylazo-pyrazole;
3,5-diamino-4-(3-hydroxy)phenylazo-pyrazole;
3,5-diamino-4-(4-hydroxy)phenylazo-pyrazole;
3,5-diamino-4-(2-hydroxymethyl)phenylazo-pyrazole;
3,5-diamino-4-(naphthyl-1-yl)azo-pyrazole; and
3,5-diamino-4-(5,6,7,8-tetrahydronaphthalene-1-yl)phenylazo-pyrazole;
and pharmaceutically acceptable salts and solvates thereof.

Another aspect of the invention relates to compounds of formula II per se, or pharmaceutically acceptable salts or solvates thereof, selected from the following:
3,5-diamino-4-(2-nitro)phenylazo-pyrazole;
3,5-diamino-4-(2,3-bis(trifluoromethyl))phenylazo-pyrazole;
3,5-diamino-4-(2,4-bis(trifluoromethyl))phenylazo-pyrazole;
3,5-diamino-4-(2,5-bis(trifluoromethyl))phenylazo-pyrazole;
3,5-diamino-4-(3,5-bis(trifluoromethyl))phenylazo-pyrazole;
3,5-diamino-4-(4-bromo-3-chloro)phenylazo-pyrazole;
3,5-diamino-4-(4-bromo-2-chloro)phenylazo-pyrazole;
3,5-diamino-4-(2-bromo-5,6-difluoro)phenylazo-pyrazole;
3,5-diamino-4-(2-bromo-4,6-difluoro)phenylazo-pyrazole;
3,5-diamino-4-(2-bromo-6-chloro-4-(trifluoromethyl))phenylazo-pyrazole;
3,5-diamino-4-(4-bromo-2,6-difluoro)phenylazo-pyrazole;
3,5-diamino-4-(4-bromo-2-fluoro)phenylazo-pyrazole;
3,5-diamino-4-(2-bromo-4-fluoro)phenylazo-pyrazole;
3,5-diamino-4-(2-bromo-4-methyl)phenylazo-pyrazole;
3,5-diamino-4-(3-bromo-2-methyl)phenylazo-pyrazole;
3,5-diamino-4-(4-bromo-3-methyl)phenylazo-pyrazole;
3,5-diamino-4-(2-bromo-4-(trifluoromethoxy)phenylazo-pyrazole;

3,5-diamino-4-(3-bromo-4-(trifluoromethoxy)phenylazo-pyrazole;
3,5-diamino-4-(4-bromo-2-(trifluoromethoxy)phenylazo-pyrazole;
3,5-diamino-4-(2-bromo-4,5,6-trifluoro)phenylazo-pyrazole;
3,5-diamino-4-(2,4-dibromo)phenylazo-pyrazole;
3,5-diamino-4-(2,5-dibromo)phenylazo-pyrazole;
3,5-diamino-4-(2,4-dibromo-3,6-dichloro)phenylazo-pyrazole;
3,5-diamino-4-(2,6-dibromo-4-fluoro)phenylazo-pyrazole;
3,5-diamino-4-(2,6-dibromo-4-(trifluoromethoxy))phenylazo-pyrazole;
3,5-diamino-4-(2,4-dibromo-6-(trifluoromethoxy))phenylazo-pyrazole;
3,5-diamino-4-(2,6-dibromo-4-(trifluoromethyl))phenylazo-pyrazole;
3,5-diamino-4-(2,6-dichloro)phenylazo-pyrazole;
3,5-diamino-4-(2,6-dichloro-4-(trifluoromethoxy))phenylazo-pyrazole;
3,5-diamino-4-(2,4-dichloro-6-(trifluoromethoxy))phenylazo-pyrazole;
3,5-diamino-4-(2,6-dichloro-4-(trifluoromethyl))phenylazo-pyrazole;
3,5-diamino-4-(2,3-difluoro)phenylazo-pyrazole;
3,5-diamino-4-(2,4-difluoro)phenylazo-pyrazole;
3,5-diamino-4-(2,5-difluoro)phenylazo-pyrazole;
3,5-diamino-4-(3,5-difluoro)phenylazo-pyrazole;
3,5-diamino-4-(2-difluoromethoxy)phenylazo-pyrazole;
3,5-diamino-4-(2-difluoromethoxy-5-nitro)phenylazo-pyrazole;
3,5-diamino-4-(2,3-difluoro-6-nitro)phenylazo-pyrazole;
3,5-diamino-4-(2,4-diiodo)phenylazo-pyrazole;
3,5-diamino-4-(2,3-dimethyl)phenylazo-pyrazole;
3,5-diamino-4-(2,3-dimethyl-6-nitro)phenylazo-pyrazole;
3,5-diamino-4-(2,3-dimethoxy)phenylazo-pyrazole;
3,5-diamino-4-(2,4-dimethoxy)phenylazo-pyrazole;
3,5-diamino-4-(2,3-dinitro-6-methyl)phenylazo-pyrazole;
3,5-diamino-4-(4-hydroxy-2-methyl)phenylazo-pyrazole;
3,5-diamino-4-(3-chloro-2,6-dibromo-4-fluoro)phenylazo-pyrazole;
3,5-diamino-4-(2-chloro-4-fluoro)phenylazo-pyrazole;
3,5-diamino-4-(2-chloro-5-fluoro)phenylazo-pyrazole;
3,5-diamino-4-(2-chloro-6-fluoro)phenylazo-pyrazole;
3,5-diamino-4-(3-chloro-2-fluoro)phenylazo-pyrazole;
3,5-diamino-4-(3-chloro-4-fluoro)phenylazo-pyrazole;
3,5-diamino-4-(4-chloro-2-fluoro)phenylazo-pyrazole;
3,5-diamino-4-(5-chloro-2-fluoro)phenylazo-pyrazole;
3,5-diamino-4-(3-chloro-4-fluoro)phenylazo-pyrazole;
3,5-diamino-4-(2-chloro-4-fluoro-5-methyl)phenylazo-pyrazole;
3,5-diamino-4-(5-chloro-4-fluoro-2-nitro)phenylazo-pyrazole;
3,5-diamino-4-(5-chloro-2-hydroxy)phenylazo-pyrazole;
3,5-diamino-4-(4-chloro-2-iodo)phenylazo-pyrazole;
3,5-diamino-4-(2-chloro-4-iodo)phenylazo-pyrazole;
3,5-diamino-4-(2-chloro-3-methyl)phenylazo-pyrazole;
3,5-diamino-4-(3-chloro-4-(trifluoromethoxy))phenylazo-pyrazole;
3,5-diamino-4-(4-chloro-2-(trifluoromethoxy))phenylazo-pyrazole;
3,5-diamino-4-(2-fluoro-4-iodo)phenylazo-pyrazole;
3,5-diamino-4-(2-fluoro-4-methyl)phenylazo-pyrazole;
3,5-diamino-4-(3-fluoro-2-methyl)phenylazo-pyrazole;
3,5-diamino-4-(2-fluoro-5-nitro)phenylazo-pyrazole;
3,5-diamino-4-(3-fluoro-5-methyl)phenylazo-pyrazole;
3,5-diamino-4-(4-fluoro-2-methyl)phenylazo-pyrazole;
3,5-diamino-4-(4-fluoro-3-methyl)phenylazo-pyrazole;
3,5-diamino-4-(5-fluoro-2-methyl)phenylazo-pyrazole;
3,5-diamino-4-(4-fluoro-2-nitro)phenylazo-pyrazole;
3,5-diamino-4-(4-fluoro-3-nitro)phenylazo-pyrazole;
3,5-diamino-4-(2-fluoro-4-(trifluoromethyl))phenylazo-pyrazole;
3,5-diamino-4-(2-iodo)phenylazo-pyrazole;
3,5-diamino-4-(2-methoxy-5-methyl)phenylazo-pyrazole;
3,5-diamino-4-(2-methoxy-6-methyl)phenylazo-pyrazole;
3,5-diamino-4-(4-methoxy-2-methyl)phenylazo-pyrazole;
3,5-diamino-4-(4-methoxy-3-(trifluoromethyl))phenylazo-pyrazole;
3,5-diamino-4-(3-methoxy-4-(trifluoromethyl)phenylazo-pyrazole;
3,5-diamino-4-(2-methyl-3-(trifluoromethoxy))phenylazo-pyrazole;
3,5-diamino-4-(2-methyl-4-(trifluoromethoxy))phenylazo-pyrazole;
3,5-diamino-4-(2-methylthio)phenylazo-pyrazole;
3,5-diamino-4-(2-nitro-4,5,6-(trifluoro)phenylazo-pyrazole;
3,5-diamino-4-(2-nitro-4-(trifluoromethoxy))phenylazo-pyrazole;
3,5-diamino-4-(2-nitrotetrafluoro)phenylazo-pyrazole;
3,5-diamino-4-(2,3,4,5,6-pentabromo)phenylazo-pyrazole;
3,5-diamino-4-(2,3,4,5-tetrachloro)phenylazo-pyrazole;
3,5-diamino-4-(2,3,5,6-tetrachloro)phenylazo-pyrazole;
3,5-diamino-4-(4-(1,1,2,2-tetrafluoroethoxy))phenylazo-pyrazole;
3,5-diamino-4-(2,3,4,5-tetrafluoro)phenylazo-pyrazole;
3,5-diamino-4-(2,3,4,6-tetrafluoro)phenylazo-pyrazole;
3,5-diamino-4-(2,3,5,6-tetrafluoro-4-(trifluoromethyl))phenylazo-pyrazole;
3,5-diamino-4-(2,4,6-tribromo)phenylazo-pyrazole;
3,5-diamino-4-(2,4,6-tribromo-3,5-diiodo)phenylazo-pyrazole;
3,5-diamino-4-(2,3,4-trichloro)phenylazo-pyrazole;
3,5-diamino-4-(2,4,5-trichloro)phenylazo-pyrazole;
3,5-diamino-4-(2,4,5-trifluoro)phenylazo-pyrazole;
3,5-diamino-4-(2,3,5-trifluoro)phenylazo-pyrazole;
3,5-diamino-4-(2,3,6-trifluoro)phenylazo-pyrazole;
3,5-diamino-4-(2-trifluoromethoxy)phenylazo-pyrazole;
3,5-diamino-4-(3-trifluoromethoxy)phenylazo-pyrazole;
3,5-diamino-4-(4-trifluoromethoxy)phenylazo-pyrazole;
3,5-diamino-4-(2,3,4-trifluoro-6-nitro)phenylazo-pyrazole;
3,5-diamino-4-(2,4,5-trimethyl)phenylazo-pyrazole;
3,5-diamino-4-(2,4,6-trimethyl)phenylazo-pyrazole;
3,5-diamino-4-(3-trimethyl)phenylazo-pyrazole;
3,5-diamino-4-(3-trichloro-5-amino)phenylazo-pyrazole;
3,5-diamino-4-(3-trichloro-4-carboxy)phenylazo-pyrazole;
3,5-diamino-4-(3-amino-4-chloro)phenylazo-pyrazole;
3,5-diamino-4-(3-chloro-4-amino)phenylazo-pyrazole;
3,5-diamino-4-(3-carboxy-4-hydroxy)phenylazo-pyrazole;
3,5-diamino-4-(naphth-1-yl)phenylazo-pyrazole;
3,5-diamino-4-(5,6,7,8-tetrahydronaphthalene-1-yl)phenylazo-pyrazole;
3-{4-[(3,5-diamino-pyrazol-4-yl)-azo]-phenyl}-1,2-dihydro-quinoxaline-2-one;
3-{2-[(3,5-diamino-pyrazol-4-yl)-azo]benzyl}-1,2-dihydro-quinoxaline-2-one;
3-{4-[(3,5-Diaminopyrazol-4-yl)-azo]-benzyl}-1,2-dihydro-quinoxaline-2-one;
3-{2-[(3,5-diamino-pyrazol-4-yl)-azo]-phenyl}-1,2-dihydro-5,6-dimethylquinoxaline-2-one;
3-{2-[(3,5-diamino-pyrazol-4-yl)-azo]-phenyl}-1,2-dihydro-5,6-dichloroquinoxaline-2-one;
3-{4-[(3,5-diamino-pyrazol-4-yl)-azo]-phenyl}-1,2-dihydro-5,6-dimethyl-quinoxaline-2-one;

3-{4-[(3,5-diamino-pyrazol-4-yl)-azo]-phenyl}-1,2-dihydro-5,6-dichloro-quinoxaline-2-one;
3-{2-[(3,5-Diamino-pyrazol-4-azo]benzyl}-1,2-dihydro-5,6-dimethyl-quinoxaline-2-one;
3-{2-[(3,5-Diamino-pyrazol-4-yl)-azo]-benzyl}-1,2-dihydro-5,6-dichloroquinoxaline-2-one;
3-{4-[(3,5-Diamino-pyrazol-4-yl)-azo]benzyl}-1,2-dihydro-5,6-dimethyl-quinoxaline-2-one;
3-{4-[(3,5-Diamino-pyrazol-4-yl)-azo]benzyl}-1,2-dihydro-5,6-dichloro-quinoxaline-2-one;
3-{3-(3,5-Dioxo-2,3,4,5-tetrahydro-[1,2,4]triazin-6-yl)-2-[(3,5-diaminopyrazol-4-yl)-azo]-phenyl}-1,2-dihydro-quinoxaline-2-one;
1,3-bis-(3,5-dioxo-2,3,4,5-tetrahydro-[1,2,4]triazin-6-yl)-2-[(3,5-diamino-pyrazol-4-yl)-azo]-benzene;
1,3-bis-(6-carboxy-3,5-dioxo-2,3,4,5-tetrahydro-[1,2,4]triazin-2-yl)-5-[(3,5-diamino-pyrazol-4-yl)-azo]-benzene;
7-[(3,5-Diamino-pyrazol-4-yl)-azo]-1,2-dihydro-quinoxaline-2-one;
4-[(pyridin-3-yl)-azo]-3,5-diamino-pyrazole;
4-[(quinoline-5-yl)-azo]-3,5-diamino-pyrazole;
4-[(quinoline-8-yl)-azo]-3,5-diamino-pyrazole;
3,5-diamino-4-(2-carboxy)phenylazo-pyrazole;
3,5-diamino-4-(3-carboxy)phenylazo-pyrazole;
3,5-diamino-4-(2-hydroxymethyl)phenylazo-pyrazole;
3,5-diamino-4-(4-aminomethyl)phenylazo-pyrazole;
3,5-diamino-4-(naphth-1-yl)azo-pyrazole; and
3,5-diamino-4-(naphth-2-yl)azo-pyrazole;
and pharmaceutically acceptable salts and solvates thereof.

In one preferred embodiment, the compound of formula II is selected from the following:
3,5-diamino-4-(2-nitro)phenylazo-pyrazole;
3,5-diamino-4-(2-hydroxymethyl)phenylazo-pyrazole;
3,5-diamino-4-(naphthyl-1-yl)azo-pyrazole; and
3,5-diamino-4-(5,6,7,8-tetrahydronaphthalene-1-yl)phenylazo-pyrazole;
and pharmaceutically acceptable salts and solvates thereof.

Another aspect of the invention relates to the use of a compound selected from the following, or a pharmaceutically acceptable salt or solvate thereof:
3,5-diamino-4-(2-hydroxy)phenylazo-pyrazole;
3,5-diamino-4-(2-nitro)phenylazo-pyrazole;
3,5-diamino-4-(3-nitro)phenylazo-pyrazole;
3,5-diamino-4-(4-nitro)phenylazo-pyrazole;
3,5-diamino-4-(2,3-bis(trifluoromethyl))phenylazo-pyrazole;
3,5-diamino-4-(2,4-bis(trifluoromethyl))phenylazo-pyrazole;
3,5-diamino-4-(2,5-bis(trifluoromethyl))phenylazo-pyrazole;
3,5-diamino-4-(3,5-bis(trifluoromethyl))phenylazo-pyrazole;
3,5-diamino-4-(4-bromo-3-chloro)phenylazo-pyrazole;
3,5-diamino-4-(4-bromo-2-chloro)phenylazo-pyrazole;
3,5-diamino-4-(2-bromo-5,6-difluoro)phenylazo-pyrazole;
3,5-diamino-4-(2-bromo-4,6-difluoro)phenylazo-pyrazole;
3,5-diamino-4-(2-bromo-6-chloro-4-(trifluoromethyl))phenylazo-pyrazole;
3,5-diamino-4-(4-bromo-2,6-difluoro)phenylazo-pyrazole;
3,5-diamino-4-(4-bromo-2-fluoro)phenylazo-pyrazole;
3,5-diamino-4-(2-bromo-4-fluoro)phenylazo-pyrazole;
3,5-diamino-4-(2-bromo-4-methyl)phenylazo-pyrazole;
3,5-diamino-4-(3-bromo-2-methyl)phenylazo-pyrazole;
3,5-diamino-4-(4-bromo-3-methyl)phenylazo-pyrazole;
3,5-diamino-4-(2-bromo-4-(trifluoromethoxy)phenylazo-pyrazole;
3,5-diamino-4-(3-bromo-4-(trifluoromethoxy)phenylazo-pyrazole;
3,5-diamino-4-(4-bromo-2-(trifluoromethoxy)phenylazo-pyrazole;
3,5-diamino-4-(2-bromo-4,5,6-trifluoro)phenylazo-pyrazole;
3,5-diamino-4-(2,4-dibromo)phenylazo-pyrazole;
3,5-diamino-4-(2,5-dibromo)phenylazo-pyrazole;
3,5-diamino-4-(2,4-dibromo-3,6-dichloro)phenylazo-pyrazole;
3,5-diamino-4-(2,6-dibromo-4-fluoro)phenylazo-pyrazole;
3,5-diamino-4-(2,6-dibromo-4-(trifluoromethoxy))phenylazo-pyrazole;
3,5-diamino-4-(2,4-dibromo-6-(trifluoromethoxy))phenylazo-pyrazole;
3,5-diamino-4-(2,6-dibromo-4-(trifluoromethyl))phenylazo-pyrazole;
3,5-diamino-4-(2,3-dichloro)phenylazo-pyrazole;
3,5-diamino-4-(2,4-dichloro)phenylazo-pyrazole;
3,5-diamino-4-(2,5-dichloro)phenylazo-pyrazole;
3,5-diamino-4-(2,6-dichloro)phenylazo-pyrazole;
3,5-diamino-4-(2,6-dichloro-4-(trifluoromethoxy))phenylazo-pyrazole;
3,5-diamino-4-(2,4-dichloro-6-(trifluoromethoxy))phenylazo-pyrazole;
3,5-diamino-4-(2,6-dichloro-4-(trifluoromethyl))phenylazo-pyrazole;
3,5-diamino-4-(2,3-difluoro)phenylazo-pyrazole;
3,5-diamino-4-(2,4-difluoro)phenylazo-pyrazole;
3,5-diamino-4-(2,5-difluoro)phenylazo-pyrazole;
3,5-diamino-4-(2-difluoromethoxy)phenylazo-pyrazole;
3,5-diamino-4-(2-difluoromethoxy-5-nitro)phenylazo-pyrazole;
3,5-diamino-4-(2,3-difluoro-6-nitro)phenylazo-pyrazole;
3,5-diamino-4-(2,4-diiodo)phenylazo-pyrazole;
3,5-diamino-4-(2,3-dimethyl)phenylazo-pyrazole;
3,5-diamino-4-(2,4-dimethyl)phenylazo-pyrazole;
3,5-diamino-4-(2,3-dimethyl-6-nitro)phenylazo-pyrazole;
3,5-diamino-4-(2,3-dimethoxy)phenylazo-pyrazole;
3,5-diamino-4-(2,4-dimethoxy)phenylazo-pyrazole;
3,5-diamino-4-(2,3-dinitro-6-methyl)phenylazo-pyrazole;
3,5-diamino-4-(4-hydroxy-2-methyl)phenylazo-pyrazole;
3,5-diamino-4-(3-chloro-2,6-dibromo-4-fluoro)phenylazo-pyrazole;
3,5-diamino-4-(2-chloro-4-fluoro)phenylazo-pyrazole;
3,5-diamino-4-(2-chloro-5-fluoro)phenylazo-pyrazole;
3,5-diamino-4-(2-chloro-6-fluoro)phenylazo-pyrazole;
3,5-diamino-4-(3-chloro-2-fluoro)phenylazo-pyrazole;
3,5-diamino-4-(3-chloro-4-fluoro)phenylazo-pyrazole;
3,5-diamino-4-(4-chloro-2-fluoro)phenylazo-pyrazole;
3,5-diamino-4-(5-chloro-2-fluoro)phenylazo-pyrazole;
3,5-diamino-4-(3-chloro-4-fluoro)phenylazo-pyrazole;
3,5-diamino-4-(2-chloro-4-fluoro-5-methyl)phenylazo-pyrazole;
3,5-diamino-4-(5-chloro-4-fluoro-2-nitro)phenylazo-pyrazole;
3,5-diamino-4-(5-chloro-2-hydroxy)phenylazo-pyrazole;
3,5-diamino-4-(4-chloro-2-iodo)phenylazo-pyrazole;
3,5-diamino-4-(2-chloro-4-iodo)phenylazo-pyrazole;
3,5-diamino-4-(2-chloro-3-methyl)phenylazo-pyrazole;
3,5-diamino-4-(3-chloro-2-methyl)phenylazo-pyrazole;
3,5-diamino-4-(3-chloro-4-(trifluoromethoxy))phenylazo-pyrazole;
3,5-diamino-4-(4-chloro-2-(trifluoromethoxy))phenylazo-pyrazole;
3,5-diamino-4-(2-fluoro-4-iodo)phenylazo-pyrazole;
3,5-diamino-4-(2-fluoro-4-methyl)phenylazo-pyrazole;

3,5-diamino-4-(3-fluoro-2-methyl)phenylazo-pyrazole;
3,5-diamino-4-(2-fluoro-5-nitro)phenylazo-pyrazole;
3,5-diamino-4-(3-fluoro-4-methyl)phenylazo-pyrazole;
3,5-diamino-4-(4-fluoro-2-methyl)phenylazo-pyrazole;
3,5-diamino-4-(4-fluoro-3-methyl)phenylazo-pyrazole;
3,5-diamino-4-(5-fluoro-2-methyl)phenylazo-pyrazole;
3,5-diamino-4-(4-fluoro-2-nitro)phenylazo-pyrazole;
3,5-diamino-4-(4-fluoro-3-nitro)phenylazo-pyrazole;
3,5-diamino-4-(2-fluoro-4-(trifluoromethyl))phenylazo-pyrazole;
3,5-diamino-4-(2-iodo)phenylazo-pyrazole;
3,5-diamino-4-(2-methoxy)phenylazo-pyrazole;
3,5-diamino-4-(2-methoxy-5-methyl)phenylazo-pyrazole;
3,5-diamino-4-(2-methoxy-6-methyl)phenylazo-pyrazole;
3,5-diamino-4-(4-methoxy-2-methyl)phenylazo-pyrazole;
3,5-diamino-4-(4-methoxy-3-(trifluoromethyl))phenylazo-pyrazole;
3,5-diamino-4-(3-methoxy-4-(trifluoromethyl)phenylazo-pyrazole;
3,5-diamino-4-(3-methyl)phenylazo-pyrazole;
3,5-diamino-4-(2-methyl-3-(trifluoromethoxy))phenylazo-pyrazole;
3,5-diamino-4-(2-methyl-4-(trifluoromethoxy))phenylazo-pyrazole;
3,5-diamino-4-(2-methylthio)phenylazo-pyrazole;
3,5-diamino-4-(2-nitro-4,5,6-(trifluoro)phenylazo-pyrazole;
3,5-diamino-4-(2-nitro-4-(trifluoromethoxy))phenylazo-pyrazole;
3,5-diamino-4-(2-nitrotetrafluoro)phenylazo-pyrazole;
3,5-diamino-4-(2,3,4,5,6-pentabromo)phenylazo-pyrazole;
3,5-diamino-4-(2,3,4,5-tetrachloro)phenylazo-pyrazole;
3,5-diamino-4-(2,3,5,6-tetrachloro)phenylazo-pyrazole;
3,5-diamino-4-(4-(1,1,2,2-tetrafluoroethoxy))phenylazo-pyrazole;
3,5-diamino-4-(2,3,4,5-tetrafluoro)phenylazo-pyrazole;
3,5-diamino-4-(2,3,4,6-tetrafluoro)phenylazo-pyrazole;
3,5-diamino-4-(2,3,5,6-tetrafluoro-4-(trifluoromethyl))phenylazo-pyrazole;
3,5-diamino-4-(2,4,6-tribromo)phenylazo-pyrazole;
3,5-diamino-4-(2,4,6-tribromo-3,5-diiodo)phenylazo-pyrazole;
3,5-diamino-4-(2,3,4-trichloro)phenylazo-pyrazole;
3,5-diamino-4-(2,4,5-trichloro)phenylazo-pyrazole;
3,5-diamino-4-(2,4,6-trichloro)phenylazo-pyrazole;
3,5-diamino-4-(2,4,5-trifluoro)phenylazo-pyrazole;
3,5-diamino-4-(2,3,5-trifluoro)phenylazo-pyrazole;
3,5-diamino-4-(2,3,6-trifluoro)phenylazo-pyrazole;
3,5-diamino-4-(2-trifluoromethoxy)phenylazo-pyrazole;
3,5-diamino-4-(3-trifluoromethoxy)phenylazo-pyrazole;
3,5-diamino-4-(4-trifluoromethoxy)phenylazo-pyrazole;
3,5-diamino-4-(2,3,4-trifluoro-6-nitro)phenylazo-pyrazole;
3,5-diamino-4-(2,4,5-trimethyl)phenylazo-pyrazole;
3,5-diamino-4-(2,4,6-trimethyl)phenylazo-pyrazole;
3,5-diamino-4-(3-trimethyl)phenylazo-pyrazole;
3,5-diamino-4-(3-trichloro-5-amino)phenylazo-pyrazole;
3,5-diamino-4-(3-trichloro-4-carboxy)phenylazo-pyrazole;
3,5-diamino-4-(3-amino-4-chloro)phenylazo-pyrazole;
3,5-diamino-4-(3-chloro-4-amino)phenylazo-pyrazole;
3,5-diamino-4-(3-carboxy-4-hydroxy)phenylazo-pyrazole;
3,5-diamino-4-(naphth-1-yl)phenylazo-pyrazole;
3,5-diamino-4-(5,6,7,8-tetrahydronaphthalene-1-yl)phenylazo-pyrazole;
N-({4-[(3,5-diamino-pyrazol-4-yl)azo]phenyl}sulfonyl)-acetamide;
N-[amino(imino)methyl]-4-[(3,5-diamino-pyrazol-4-yl)azo]-benzansulfonamide;
4-[(3,5-diaminopyrazol-4-yl)azo]-N-(thiazol-2-yl)-benzensulfonamide;
4-[(3,5-diamino-pyrazol-4-yl)-azo]-N-(4,6-dimethylpyrimidin-2-yl)benzensulfonamide;
4-[(3,5-diamino-pyrazol-4-yl)-azo]-N-(5-methoxypyrimidin-2-yl)-benzensulfonamide;
4-[(3,5-diamino-pyrazol-4-yl)-azo]-N-(6-methoxypyridazin-3-yl)-benzensulfonamide;
3-{2-[(3,5-diamino-pyrazol-4-yl)-azo]-phenyl}-1,2-dihydroquinoxaline-2-one;
3-{4-[(3,5-diamino-pyrazol-4-yl)-azo]-phenyl}-1,2-dihydro-quinoxaline-2-one;
3-{2-[(3,5-diamino-pyrazol-4-yl)-azo]benzyl}-1,2-dihydro-quinoxaline-2-one;
3-{4-[(3,5-Diaminopyrazol-4-yl)-azo]-benzyl}-1,2-dihydro-quinoxaline-2-one;
3-{2-[(3,5-diamino-pyrazol-4-yl)-azo]-phenyl}-1,2-dihydro-5,6-dimethylquinoxaline-2-one;
3-{2-[(3,5-diamino-pyrazol-4-yl)-azo]-phenyl}-1,2-dihydro-5,6-dichloro-quinoxaline-2-one;
3-{4-[(3,5-diamino-pyrazol-4-yl)-azo]-phenyl}-1,2-dihydro-5,6-dimethyl-quinoxaline-2-one;
3-{4-[(3,5-diamino-pyrazol-4-yl)-azo]-phenyl}-1,2-dihydro-5,6-dichloro-quinoxaline-2-one;
3-{2-[(3,5-Diamino-pyrazol-4-azo]benzyl}-1,2-dihydro-5,6-dimethyl-quinoxaline-2-one;
3-{2-[(3,5-Diamino-pyrazol-4-yl)-azo]-benzyl}-1,2-dihydro-5,6-dichloroquinoxaline-2-one;
3-{4-[(3,5-Diamino-pyrazol-4-yl)-azo]benzyl}-1,2-dihydro-5,6-dimethyl-quinoxaline-2-one;
3-{4-[(3,5-Diamino-pyrazol-4-yl)-azo]benzyl}-1,2-dihydro-5,6-dichloro-quinoxaline-2-one;
3-{3-(3,5-Dioxo-2,3,4,5-tetrahydro-[1,2,4]triazin-6-yl)-2-[(3,5-diaminopyrazol-4-yl)-azo]-phenyl}-1,2-dihydro-quinoxaline-2-one;
1,3-bis-(3,5-dioxo-2,3,4,5-tetrahydro-[1,2,4]triazin-6-yl)-2-[(3,5-diamino-pyrazol-4-yl)-azo]-benzene;
1,3-bis-(6-carboxy-3,5-dioxo-2,3,4,5-tetrahydro-[1,2,4]triazin-2-yl)-5-[(3,5-diamino-pyrazol-4-yl)-azo]-benzene;
7-[(3,5-Diamino-pyrazol-4-yl)-azo]-1,2-dihydro-quinoxaline-2-one;
4-[(pyridin-3-yl)-azo]-3,5-diamino-pyrazole;
4-[(quinoline-5-yl)-azo]-3,5-diamino-pyrazole;
4-[(quinoline-8-yl)-azo]-3,5-diamino-pyrazole;
3,5-diamino-4-(2-carboxy)phenylazo-pyrazole;
3,5-diamino-4-(3-carboxy)phenylazo-pyrazole;
3,5-diamino-4-(2-hydroxymethyl)phenylazo-pyrazole;
3,5-diamino-4-(4-aminomethyl)phenylazo-pyrazole;
3,5-diamino-4-(naphth-1-yl)azo-pyrazole;
3,5-diamino-4-(naphth-2-yl)azo-pyrazole;
in the preparation of a medicament for treating a proliferative disorder.

Preferably, for this aspect (antiproliferative), the compound of formula II is selected from the following:
3,5-diamino-4-(2-nitro)phenylazo-pyrazole;
3,5-diamino-4-(3-nitro)phenylazo-pyrazole;
3,5-diamino-4-(4-nitro)phenylazo-pyrazole;
3,5-diamino-4-(2-hydroxy)phenylazo-pyrazole;
3,5-diamino-4-(2-hydroxymethyl)phenylazo-pyrazole;
3,5-diamino-4-(naphthyl-1-yl)azo-pyrazole;
3,5-diamino-4-(5,6,7,8-tetrahydronaphthalene-1-yl)phenylazo-pyrazole;
and pharmaceutically acceptable salts and solvates thereof.

The novel compounds of this invention per se or as intermediates in the preparation of novel compound having a wide variety of industrial utilities.

Therapeutic Use

The compounds of the present invention have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29 or Saos-2 Using such assays it may be determined whether a compound is anti-proliferative in the context of the present invention.

One preferred embodiment of the present invention therefore relates to the use of one or more compounds of the invention in the preparation of a medicament for treating a proliferative disorder.

As used herein the phrase "preparation of a medicament" includes the use of a compound of the invention directly as the medicament in addition to its use in a screening programme for further therapeutic agents or in any stage of the manufacture of such a medicament.

Preferably, the proliferative disorder is a cancer or leukaemia. The term proliferative disorder is used herein in a broad sense to include any disorder that requires control of the cell cycle, for example cardiovascular disorders such as restenosis, cardiomyopathy and myocardial infarction, auto-immune disorders such as glomerulonephritis and rheumatoid arthritis, dermatological disorders such as psoriasis, anti-inflammatory, anti-fungal, antiparasitic disorders such as malaria, emphysema, alopecia, and chronic obstructive pulmonary disorder. In these disorders, the compounds of the present invention may induce apoptosis or maintain stasis within the desired cells as required.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment of the invention, the compound of the invention is administered in an amount sufficient to inhibit at least one CDK enzyme.

In one preferred embodiment, the compound of the invention is capable of selectively inhibiting one or more CDK enzymes (CDK1, CDK2, CDK3, CDK4, CDK5, CDK6, CDK7, CDK8, CDK9).

Preferably, the compound of the invention is administered in an amount sufficient to inhibit at least one of CDK and/or CDK4.

One preferred embodiment of the invention relates to a method for inhibiting CDKs and cell proliferation and/or for inducing apoptosis comprising administering an effective amount of a compound of formula I or II to a subject in need thereof.

Another aspect of the invention relates to the use of a compound of the invention in the preparation of a medicament for treating a viral disorder, such as human cytomegalovirus (HCMV), herpes simplex virus type 1 (HSV-1), human immunodeficiency virus type 1 (HIV-1), and varicella zoster virus (VZV).

4-Arylazo-3,5-diamino-pyrazole derivatives result in the acquisition of extremely high potency against viruses on the part of the defined compounds. An important aspect of the present invention is a method for inhibiting proliferation of a DNA virus dependent upon events associated with cell proliferation for replication. The DNA virus includes any of the retrovirus family. The effective amount is that sufficient to inhibit cellular CDK activity to extent impending viral replication.

In a more preferred embodiment of the invention, the compound of the invention is administered in an amount sufficient to inhibit one or more of the host cell CDKs involved in viral replication, i.e. CDK2, CDK7, CDK8, and CDK9.

As defined herein, an anti-viral effect within the scope of the present invention may be demonstrated by the ability to inhibit CDK2, CDK7, CDK8 or CDK9.

In a particularly preferred embodiment, the invention relates to the use of one or more compounds of the invention in the treatment of a viral disorder which is CDK dependent or sensitive. CDK dependent disorders are associated with an above normal level of activity of one or more CDK enzymes. Such disorders preferably associated with an abnormal level of activity of CDK2, CDK7, CDK8 and/or CDK9. A CDK sensitive disorder is a disorder in which an aberration in the CDK level is not the primary cause, but is downstream of the primary metabolic aberration. In such scenarios, CDK2, CDK7, CDK8 and/or CDK9 can be said to be part of the sensitive metabolic pathway and CDK inhibitors may therefore be active in treating such disorders.

Another preferred embodiment of the invention relates to the use of a compound of formula I or II as an antimitotic compound for treatment of proliferative diseases.

In addition to therapeutic applications it will be apparent the subject compounds can be used as a cell culture additive for controlling proliferative and/or differentiation states of cells in vitro, for instance, by controlling the level of activation of a CDK. By preventing the activation of a $G_0/G_1$ CDK, the subject inhibitors can prevent mitotic progression and hence provide a means for ensuring an adequately restrictive environment in order to maintain cells at various stages of differentiations, and can be employed, for instance, in cell cultures designed to test the specific activities of trophic factors. Other tissue culture systems which require maintenance of differentiation will be readily apparent to those skilled in the art.

It is likely that inhibition by the compounds, of the invention of the catalytic activity of cyclin-dependent kinases in mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated hyperactive, form of the kinase and situations in which the kinase is present at excessive levels. Such compounds can also block excessive kinase activity in situations in which the cyclin regulating the kinase is present at excessive levels or its binding to the kinase is enhanced. Furthermore, compounds which block kinase activity by interacting with the ATP binding site of the enzyme are also useful for inhibiting kinase activity in situations in which a natural inhibitor of cyclin-kinase complexes is mutated.

It will also be apparent that differential screening assays can be used to select for those compounds of the present invention with specificity for CDK enzymes. Thus, compounds, which act specifically on eukaryotic pathogens, e.g., are anti-fungal or anti-parasitic agents, can be selected from the subject of the inhibitors.

In still another embodiment, the invention relates to the use of a compound of formula I or II for treating fungal infections (fungi) in humans, animals and plants.

By way of illustration, the assays described in the art can be used to screen for agents which may ultimately be useful for inhibiting at least one fungus implicated in such mycosis as aspergillosis, blastomycosis, chromoblastomycosis, coccidiomycosis, conidiosporosis, actinomycosis, penicilliosis, monoliasis, or sporotrichosis. For example, if the mycotic infection to which treatment is desired is aspergillosis, an assay as described above or in the appended examples can comprise comparing the relative effectiveness of a test compound on inhibiting a plant CDK enzyme with its effectiveness towards a CDK enzyme from yeast. Likewise, the differential screening assays can be used to identify anti-fungal agents which may have value in the treatment of aspergillosis by making use of the CDK genes cloned from yeast such as *Aspergillus fumigatus, Aspergillus flavus, Aspergillus niger, Aspergillus nidulans*, or *Apergillus terreus*.

In yet another embodiment, certain of the subject CDK inhibitors can be selected on the basis of inhibitory specificity for plant CDKs relative to the mammalian enzyme. For example, a plant CDK can be disposed in a differential screen with one or more of the human enzymes to select those compounds of greatest selectivity for inhibiting the plant enzyme. Thus, the present invention specifically contemplates formulations of the subject CDK inhibitors for agricultural applications, such as in the form of a defoliant or the like.

Another aspect of the invention relates to the use of compounds of the invention, or pharmaceutically acceptable salts thereof, in the preparation of a medicament for treating diabetes.

In a particularly preferred embodiment, the diabetes is type II diabetes.

GSK3 is one of several protein kinases that phosphorylate glycogen synthase (GS). The stimulation of glycogen synthesis by insulin in skeletal muscle results from the dephosphorylation and activation of GS. GSK3's action on GS thus results in the latter's deactivation and thus suppression of the conversion of glucose into glycogen in muscles.

Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes. Furthermore, it has been demonstrated that GSK3 is over-expressed in muscle cells of type II diabetics and that an inverse correlation exists between skeletal muscle GSK3 activity and insulin action.

GSK3 inhibition is therefore of therapeutic significance in the treatment of diabetes, particularly type II, and diabetic neuropathy.

It is notable that GSK3 is known to phosphorylate many substrates other than GS, and is thus involved in the regulation of multiple biochemical pathways. For example, GSK is highly expressed in the central and peripheral nervous systems.

Another aspect of the invention therefore relates to the use of compounds of the invention, or pharmaceutically acceptable salts thereof, in the preparation of a medicament for treating a CNS disorders, for example neurodegenerative disorders.

Preferably, the CNS disorder is Alzheimer's disease.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages.

Without wishing to be bound by theory, it is believed that GSK3 inhibitors may be able to prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of fronto-temporal dementia, further underscoring the relevance of tau protein dysfunction for the neurodegenerative process.

Another aspect of the invention relates to the use of compounds of the invention, or pharmaceutically acceptable salts thereof, in the preparation of a medicament for treating bipolar disorder.

Yet another aspect of the invention relates to the use of compounds of the invention, or pharmaceutically acceptable salts thereof, in the preparation of a medicament for treating a stroke.

Reducing neuronal apoptosis is an important therapeutic goal in the context of head trauma, stroke, epilepsy, and motor neuron disease. Therefore, GSK3 as a pro-apoptotic factor in neuronal cells makes this protein kinase an attractive therapeutic target for the design of inhibitory drugs to treat these diseases.

Yet another aspect of the invention relates to the use of compounds of the invention, or pharmaceutically acceptable salts thereof, in the preparation of a medicament for treating alopecia.

Hair growth is controlled by the Wnt signalling pathway, in particular Wnt-3. In tissue-culture model systems of the skin, the expression of non-degradable mutants of β-catenin leads to a dramatic increase in the population of putative stem cells, which have greater proliferative potential. This population of stem cells expresses a higher level of non-cadherin-associated β-catenin, which may contribute to their high proliferative potential. Moreover, transgenic mice overexpressing a truncated β-catenin in the skin undergo de novo hair-follicle morphogenesis, which normally is only established during embryogenesis. The ectopic application of GSK3 inhibitors may therefore be therapeutically useful in the treatment of baldness and in restoring hair growth following chemotherapy-induced alopecia.

A further aspect of the invention relates to a method of treating a GSK3-dependent disorder, said method comprising administering to a subject in need thereof, a compound according to the invention, or a pharmaceutically acceptable salt thereof, as defined above in an amount sufficient to inhibit GSK3.

Preferably, the compound of the invention, or pharmaceutically acceptable salt thereof, is administered in an amount sufficient to inhibit GSK3β.

In one embodiment of the invention, the compound of the invention is administered in an amount sufficient to inhibit at least one PLK enzyme.

The polo-like kinases (PLKs) constitute a family of serine/threonine protein kinases. Mitotic *Drosophila melanogaster* mutants at the polo locus display spindle abnormalities and polo was found to encode a mitotic kinase. In humans, there exist three closely related PLKs. They contain a highly homologous amino-terminal catalytic kinase domain and their carboxyl termini contain two or three conserved regions, the polo boxes. The function of the polo boxes remains incompletely understood but they are implicated in the targeting of PLKs to subcellular compartments, mediation of interactions with other proteins, or may constitute part of an autoregulatory domain. Furthermore, the polo box-dependent PLK1 activity is required for proper metaphase/anaphase transition and cytokinesis.

Studies have shown that human PLKs regulate some fundamental aspects of mitosis. In particular, PLK1 activity is believed to be necessary for the functional maturation of centrosomes in late G2/early prophase and subsequent establishment of a bipolar spindle. Depletion of cellular PLK1 through the small interfering RNA (siRNA) technique has also confirmed that this protein is required for multiple mitotic processes and completion of cytokinesis.

In a more preferred embodiment of the invention, the compound of the invention is administered in an amount sufficient to inhibit PLK1.

Of the three human PLKs, PLK1 is the best characterized; it regulates a number of cell division cycle effects, including the onset of mitosis, DNA-damage checkpoint activation, regulation of the anaphase promoting complex, phosphorylation of the proteasome, and centrosome duplication and maturation.

Specifically, initiation of mitosis requires activation of M-phase promoting factor (MPF), the complex between the cyclin dependent kinase CDK1 and B-type cyclins. The latter accumulate during the S and G2 phases of the cell cycle and promote the inhibitory phosphorylation of the MPF complex by WEE1, MIK1, and MYT1 kinases. At the end of the G2 phase, corresponding dephosphorylation by the dual-specificity phosphatase CDC25C triggers the activation of MPF. In interphase, cyclin B localizes to the cytoplasm, it then becomes phosphorylated during prophase and this event causes nuclear translocation. The nuclear accumulation of active MPF during prophase is thought to be important for initiating M-phase events. However, nuclear MPF is kept inactive by WEE1 unless counteracted by CDC25C. The phosphatase CDC25C itself, localized to the cytoplasm during interphase, accumulates in the nucleus in prophase. The nuclear entry of both cyclin B and CDC25C are promoted through phosphorylation by PLK1. This kinase is an important regulator of M-phase initiation.

In one particularly preferred embodiment, the compounds of the invention are ATP-antagonistic inhibitors of PLK1.

In the present context ATP antagonism refers to the ability of an inhibitor compound to diminish or prevent PLK catalytic activity, i.e. phosphotransfer from ATP to a macromolecular PLK substrate, by virtue of reversibly or irreversibly binding at the enzyme's active site in such a manner as to impair or abolish ATP binding.

In another preferred embodiment, the compound of the invention is administered in an amount sufficient to inhibit PLK2 and/or PLK3.

Mammalian PLK2 (also known as SNK) and PLK3 (also known as PRK and FNK) were originally shown to be immediate early gene products. PLK3 kinase activity appears to peak during late S and G2 phase. It is also activated during DNA damage checkpoint activation and severe oxidative stress. PLK3 also plays an important role in the regulation of microtubule dynamics and centrosome function in the cell and deregulated PLK3 expression results in cell cycle arrest and apoptosis. PLK2 is the least well understood homologue of the three PLKs. Both PLK and PLK3 may have additional important post-mitotic functions.

Pharmaceutical Compositions

Another aspect of the invention relates to a pharmaceutical composition comprising a compound of the invention as defined above admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, the one or more compounds of the invention are administered in combination with one or more other therapeutically active agents, for example, existing drugs available on the market. In such cases, the compounds of the invention may be administered consecutively, simultaneously or sequentially with the one or more other active agents.

By way of example, it is known that anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

Assays

Another aspect of the invention relates to the use of a compound of the invention in an assay for identifying further candidate compounds capable of inhibiting one or more protein kinases.

Preferably, the assay is a competitive binding assay.

More preferably, the competitive binding assay comprises contacting a compound of the invention with a protein kinase and a candidate compound and detecting any change in the interaction between the compound of the invention and the protein kinase.

One aspect of the invention relates to a process comprising the steps of:

(a) performing an assay method described hereinabove;
(b) identifying one or more ligands capable of binding to a ligand binding domain; and
(c) preparing a quantity of said one or more ligands.

Another aspect of the invention provides a process comprising the steps of:

(a) performing an assay method described hereinabove;
(b) identifying one or more ligands capable of binding to a ligand binding domain; and
(c) preparing a pharmaceutical composition comprising said one or more ligands.

Another aspect of the invention provides a process comprising the steps of:

(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of proliferative disorders, viral disorders, a CNS disorder, stroke, alopecia and diabetes.

Preferably, said candidate compound is generated by conventional SAR modification of a compound of the invention.

As used herein, the term "conventional SAR modification" refers to standard methods known in the art for varying a given compound by way of chemical derivatisation.

The above methods may be used to screen for a ligand useful as an inhibitor of one or more protein kinases.

Synthesis

Compounds of formula I and II described above can be synthesised by the routes set forth in Schemes 1A and 1B set forth below.

Scheme 1A

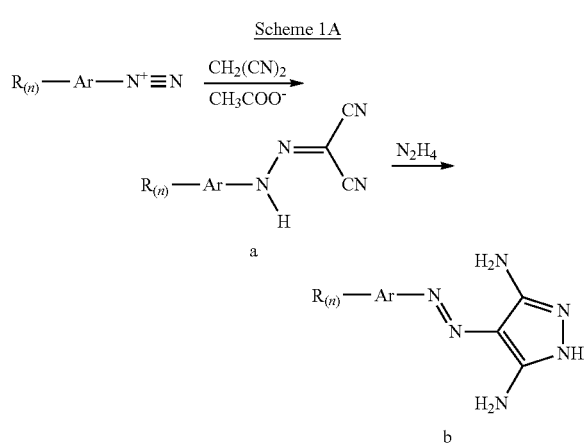

In one approach (Scheme 1A) the 4-arylazo-3,5-diamino-pyrazoles of formula (b), where R, Ar, and n are defined above for a compound of the formula I, are prepared from the appropriate hydrazones (a) after heating with methanolic solution of hydrazine hydrate. The hydrazones (a) are synthesised by diazotization of corresponding aromatic amines and followed by reaction with malononitrile in an aqueous solution of sodium acetate.

Dimeric compounds of formula (d) can be prepared in a similar manner (Scheme 1B) by using the corresponding diamine precursors.

Scheme 1B

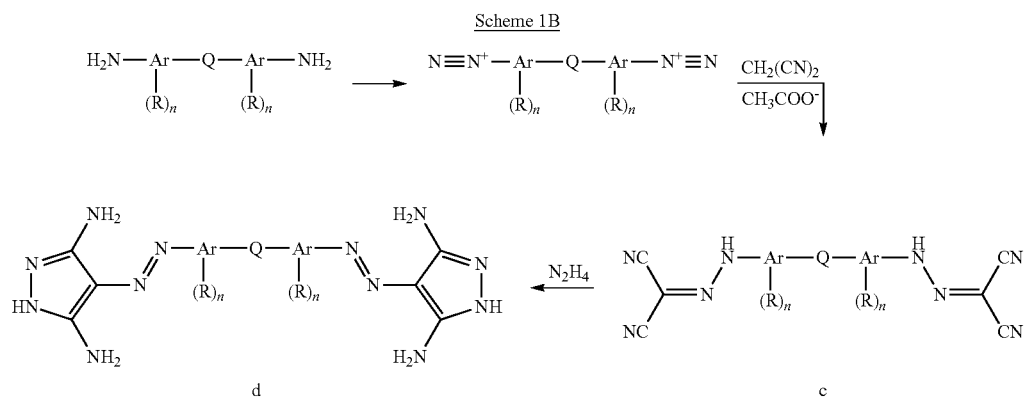

Thus, a further aspect of the invention relates to a process for preparing a compound of formula I as defined above, said process comprising the steps of:

(i) converting an amine of formula (e) to the corresponding diazonium compound (f);

(ii) reacting diazonium compound (f) with malononitrile and sodium acetate to form a compound of formula (c);

(iii) converting said compound of formula (c) to a diaminopyrazole of formula (d)

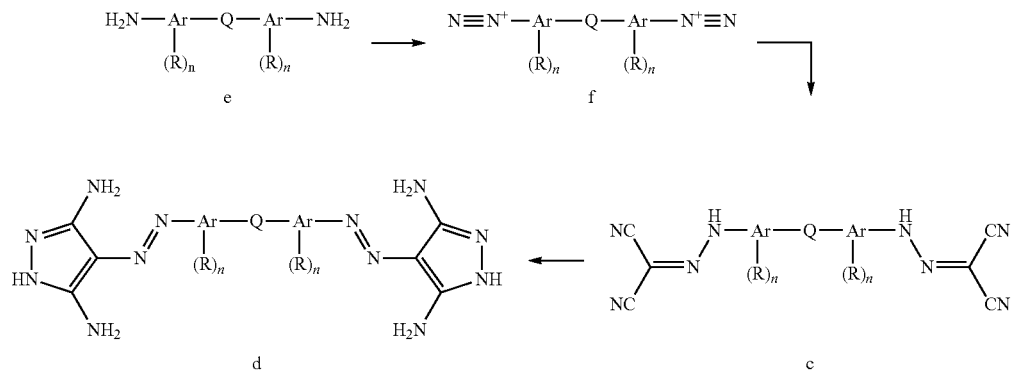

Preferably, step (i) comprises treating the amine of formula (e) with NaNO₂/HCl.

Preferably, step (iii) comprises treating said compound of formula (c) with N₂H₄.

The present invention is further described by way of example and with reference to the following figures wherein:

EXAMPLES

Figure 1:
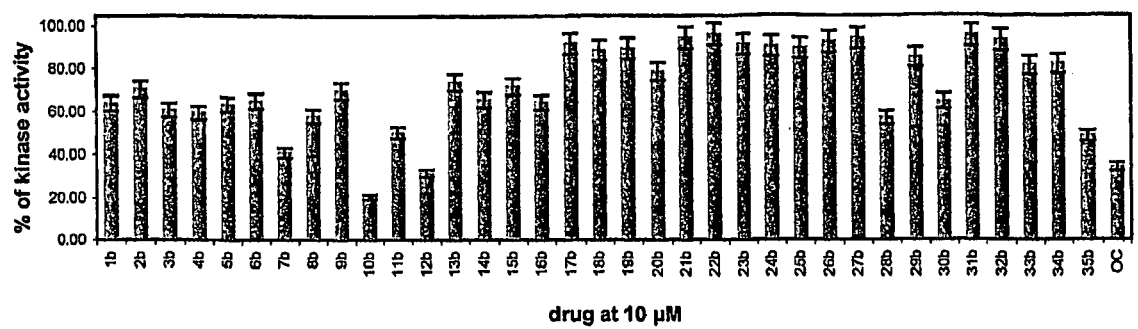
FIG. 1 shows a diagram displaying inhibition of CDK2/cyclin E by 4-arylazo-3,5-diamino-pyrazoles at 10 μM concentration and olomoucine (OC) as a control. All values are averaged from triplicates.
Figure 2:
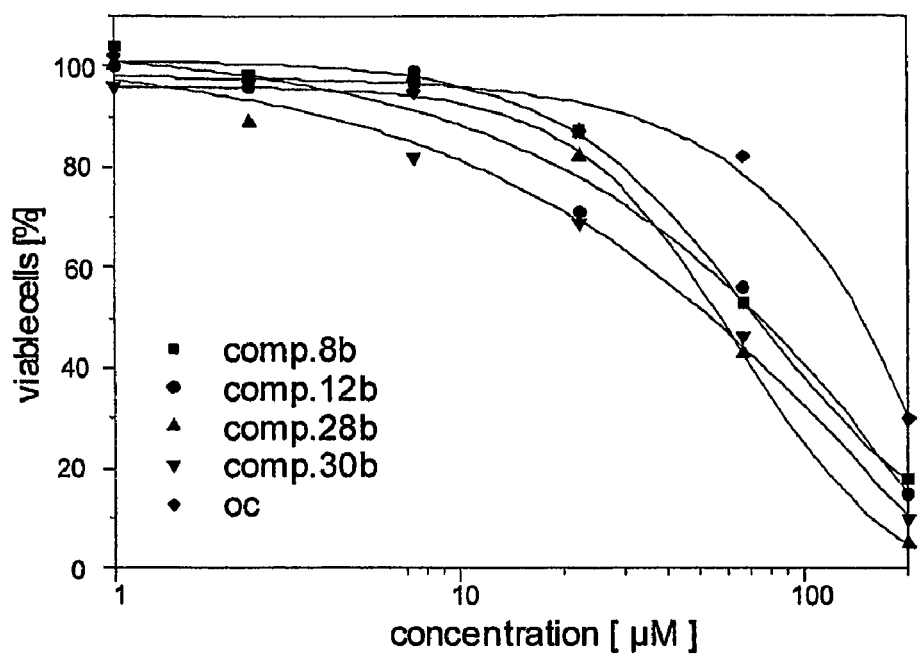
FIG. 2 shows inhibition of growth of K562 (A) and MCF7 (B) tumour cell lines by different 4-arylazo-3,5-diaminopyrazoles. Cytotoxicity was determined using Calcein AM and Fluoroskan Ascent.
Figure 2:
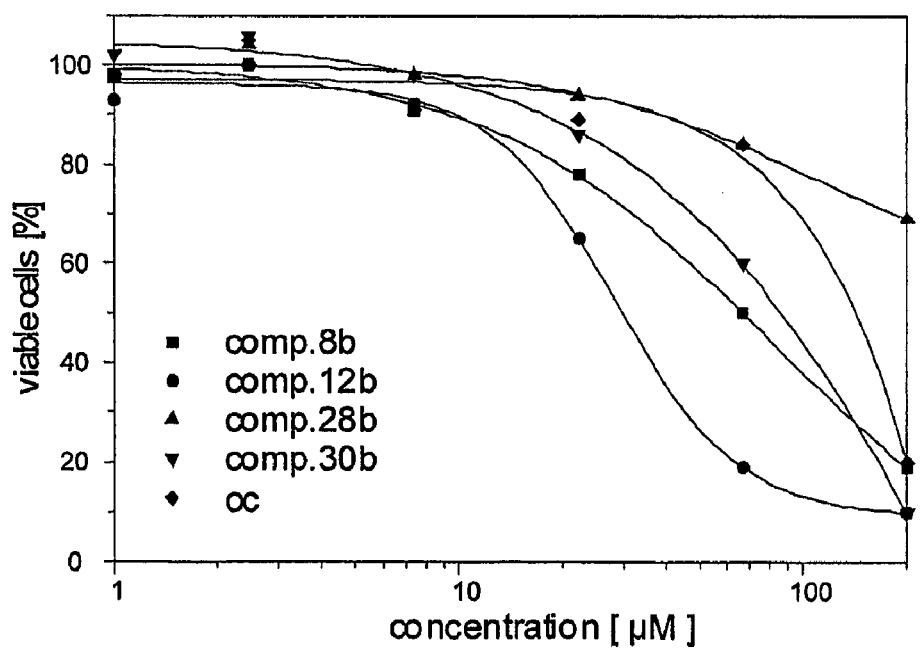

The starting material for the compounds of the formula I and II are available from commercial sources (Sigma, Aldrich, Fluka, etc.). Melting points were determined on a Koffler block and are uncorrected. Evaporations were carried out on a rotary evaporator under vacuum at temperatures below 80° C. The ¹H NMR spectra (σ, ppm; J, Hz) were measured on Varian VXR-400 (400 MHz) or on Varian Unity 300 (400 MHz) instruments. All spectra were obtained at 25° C. using tetramethylsilane as an internal standard. Electron impact mass spectra m/z (rel. %, composition, deviation) were measured on a VG 7070E spectrometer (70 eV, 200° C., direct inlet). Quadrupole mass spectra were measured on a Micromass ZMD detector with electrospray ionization. Merck silica gel Kieselgel 60 (230-400 mesh) was used for column chromatography. All compounds gave satisfactory elemental analyses (±0.4%).

Example 1

5 mmol of amine was dissolved in 30 ml of water and 4.5 ml of (37%) hydrochloric acid. A solution of 0.35 g (5 mmol) NaNO₂ in 5 ml of ice water was added dropwise to a stirred ice-cooled solution (0-5° C.) of amine. The diazonium salt so prepared was added dropwise to a solution of 0.5 g (7.5 mmol) malononitrile and 12.5 g sodium acetate in 50 ml of water with continuous stirring and cooling for 30 min. The reaction mixture was then placed into a refrigerator. The next day precipitated hydrazone was filtered off, washed with water and dried. Yields were between 90-100%. Note: for compounds 32c-35c 9 ml (37%) hydrochloride acid, 0.7 g NaNO₂, 1 g malononitrile and 25 g sodium acetate was used. Compounds prepared by this approach are shown in Schemes 2 and 3, and Tables 1 and 2 below.

Scheme 2: Synthesis of 4-arylazo-3,5-diamino-pyrazoles

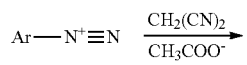

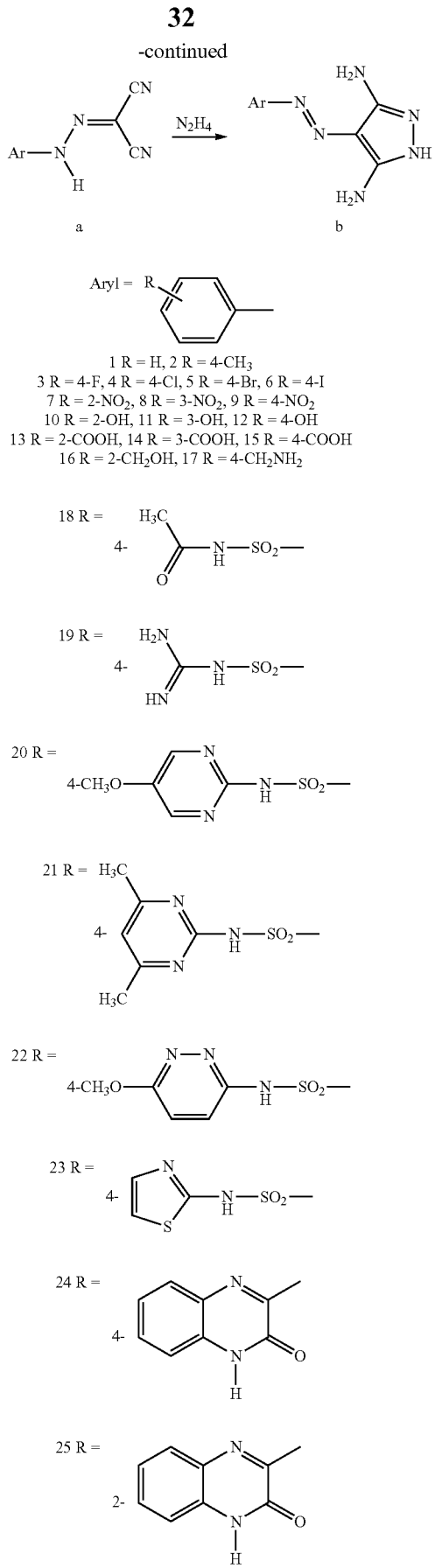

-continued

26 R =

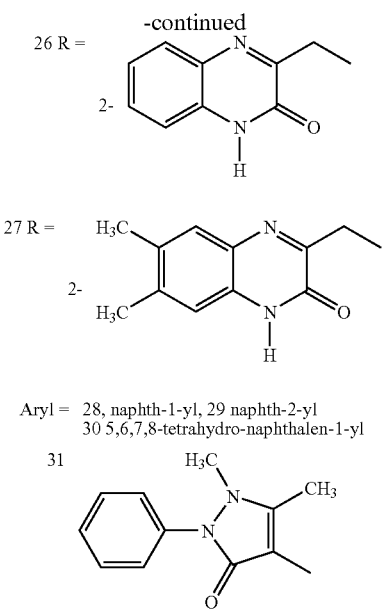

27 R =

Aryl = 28, naphth-1-yl, 29 naphth-2-yl
30 5,6,7,8-tetrahydro-naphthalen-1-yl

31

Scheme 3: Synthesis of 4-arylazo-3,5-diamino-pyrazole dimers

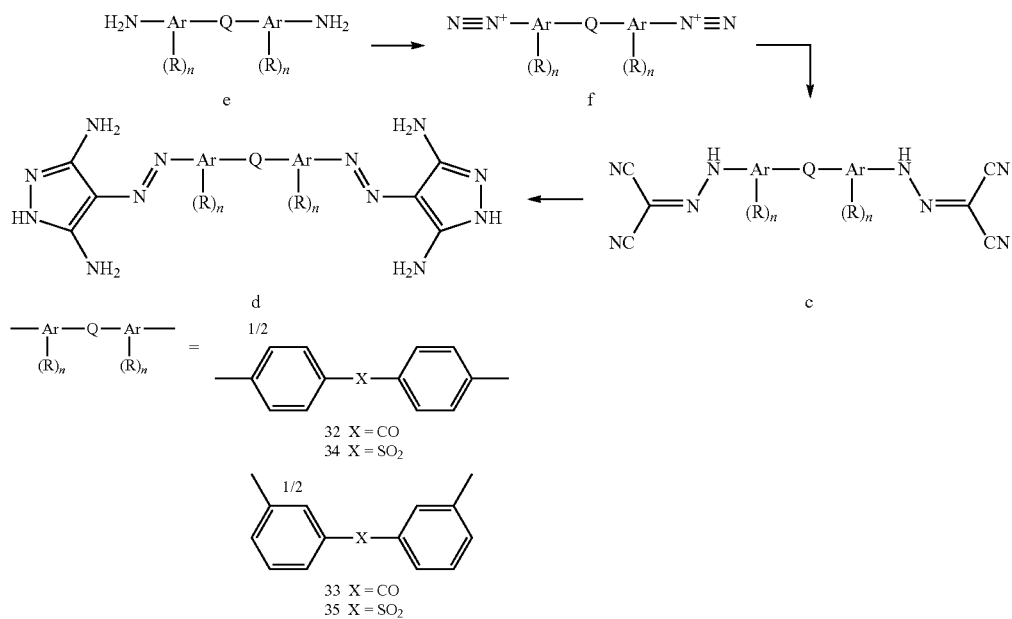

TABLE 1

Analytical data of newly prepared hydrazones.
Structures are given above.

| Comp. | Molecular formula/ weight | % Elemental analysis (calc./found) | | | mp [° C.] |
|---|---|---|---|---|---|
| | | C | H | N | |
| 6a | $C_9H_5IN_4$ 296.07 | 36.51 36.33 | 1.71 1.54 | 18.92 18.67 | 200-202 |
| 16a | $C_{10}H_8N_4O$ 200.20 | 60.00 59.97 | 4.03 3.90 | 27.99 27.59 | 118-120 |

TABLE 1-continued

Analytical data of newly prepared hydrazones.
Structures are given above.

| Comp. | Molecular formula/ weight | % Elemental analysis (calc./found) | | | mp [° C.] |
|---|---|---|---|---|---|
| | | C | H | N | |
| 17a | $C_{10}H_9N_5 \cdot HCl$ 235.68 | 50.96 51.01 | 4.28 4.07 | 29.72 29.43 | >360 |
| 24a | $C_{17}H_{10}N_6O$ 314.31 | 64.96 65.12 | 3.21 3.33 | 26.74 26.81 | 198-200 |
| 25a | $C_{17}H_{10}N_6O$ 314.31 | 64.96 65.10 | 3.21 3.43 | 26.74 26.91 | 200-201 |
| 26a | $C_{18}H_{12}N_6O$ 328.34 | 65.85 65.90 | 3.68 3.71 | 25.60 25.73 | 203-204 |
| 27a | $C_{20}H_{16}N_6O$ 356.39 | 67.40 67.24 | 4.52 4.31 | 23.58 23.66 | 207-208 |
| 28a | $C_{13}H_8N_4$ 220.24 | 70.90 70.86 | 3.66 3.33 | 25.44 25.42 | 151-153 |
| 30a | $C_{13}H_{12}N_4$ 224.27 | 69.62 69.63 | 5.39 5.11 | 24.98 24.69 | 139-142 |
| 32c | $C_{19}H_{10}N_8O$ 366.34 | 62.29 62.14 | 2.75 2.42 | 30.59 30.27 | >360 |
| 33c | $C_{19}H_{10}N_8O$ 366.34 | 62.29 62.00 | 2.75 2.84 | 30.59 30.33 | 209-212 |

TABLE 1-continued

Analytical data of newly prepared hydrazones.
Structures are given above.

| Comp. | Molecular formula/ weight | % Elemental analysis (calc./found) | | | mp [° C.] |
|---|---|---|---|---|---|
| | | C | H | N | |
| 35c | $C_{18}H_{10}N_8O_2S \cdot H_2O$ 420.41 | 51.43 51.19 | 2.88 2.68 | 26.66 26.28 | 145-147 |

TABLE 2

Analytical data of newly prepared pyrazoles.

| Comp. | Molecular formula/ weight | % Elemental analysis (calc./found) C | H | N | mp [° C.] | Recr. solvent | Yield [%] |
|---|---|---|---|---|---|---|---|
| 3b | $C_9H_9N_6F$ 220.22 | 49.09 48.91 | 4.12 3.85 | 38.17 38.47 | 272-275 | MeOH | 88 |
| 6b | $C_9H_9IN_6$ 328.13 | 32.95 33.10 | 2.76 2.60 | 25.61 25.94 | 290-292 | MeOH | 49 |
| 11b | $C_9H_{10}N_6O$ 218.22 | 49.54 49.71 | 4.62 4.84 | 38.51 38.42 | 238-240 | $H_2O$ | 42 |
| 13b | $C_{10}H_{10}N_6O_2$ 246.23 | 48.78 48.57 | 4.09 3.95 | 34.13 34.23 | 291 | $H_2O^a$ | 80 |
| 14b | $C_{10}H_{10}N_6O_2 \cdot HCl$ 282.69 | 42.49 42.25 | 3.92 3.93 | 29.73 29.51 | 245-247 | $H_2O^a$ | 82 |
| 16b | $C_{10}H_{12}N_6O$ 232.06 | 51.72 51.67 | 5.21 5.45 | 36.19 36.14 | 188-190 | $H_2O$ | 85 |
| 17b | $C_{10}H_{13}N_7$ 231.28 | 51.94 52.12 | 5.67 5.82 | 42.40 42.55 | >360 | $H_2O$ | 59 |
| 24b | $C_{17}H_{14}N_8O$ 346.37 | 58.95 59.00 | 4.07 4.20 | 32.05 32.43 | 248-249 | EtOH:$H_2O$ (1:1) | 93 |
| 25b | $C_{17}H_{14}N_8O$ 346.37 | 58.95 59.16 | 4.07 4.00 | 32.35 32.55 | 254-255 | EtOH:$H_2O$ (1:1) | 91 |
| 26b | $C_{18}H_{14}N_8O$ 360.4 | 59.99 60.10 | 4.47 4.62 | 31.09 30.94 | 241-242 | EtOH | 90 |
| 27b | $C_{20}H_{20}N_8O$ 388.45 | 61.84 61.93 | 5.19 5.02 | 28.55 28.72 | 263-264 | EtOH:$H_2O$ (1:1) | 96 |
| 28b | $C_{13}H_{12}N_6$ 252.3 | 61.89 61.67 | 4.79 4.92 | 33.31 33.41 | 198-200 | EtOH:$H_2O$ (2:1) | 36 |
| 29b | $C_{13}H_{12}N_6$ 252.3 | 61.89 61.79 | 4.79 4.52 | 33.31 33.01 | 288-290 | EtOH:$H_2O$ (2:1) | 84 |
| 30b | $C_{13}H_{16}N_6$ 256.33 | 60.92 61.19 | 6.29 6.37 | 32.79 32.44 | 186-188 | EtOH:$H_2O$ (1:2) | 95 |
| 32d | $C_{19}H_{18}N_{12}O$ 430.44 | 53.02 52.97 | 4.22 4.15 | 39.05 39.15 | >360 | EtOH:$H_2O$ (1:2) | 75 |
| 33d | $C_{19}H_{18}N_{12}O \cdot \frac{1}{2}H_2O$ 439.46 | 51.93 51.86 | 4.36 4.07 | 38.25 37.97 | 301-302 | EtOH:$H_2O$ (1:2) | 85 |
| 34d | $C_{18}H_{18}N_{12}O_2S$ 466.49 | 46.35 46.19 | 3.89 3.79 | 36.03 35.94 | 330-332 | EtOH:$H_2O$ (1:2) | 83 |
| 35d | $C_{18}H_{18}N_{12}O_2S$ 466.49 | 46.35 46.23 | 3.89 3.91 | 36.03 36.11 | 268-270 | EtOH:$H_2O$ (1:2) | 69 |

$^a$Precipitated by acidifying (for details see the experimental section

Example 2

CDK Inhibition Assays

CDK1/cyclin B and CDK2/cyclin E kinases were produced in Sf9 insect cells coinfected with appropriate baculoviral constructs. The cells were harvested 70 h post infection, incubated in lysis buffer (50 mM Tris pH 7.4, 150 mM NaCl, 5 mM EDTA, 20 mM NaF, 1% Tween 20, 1 mM DTT, 0.1 mM PMSF, 0.5 μg/ml leupeptine, 1 μg/ml aprotonine) for 30 min on ice and the soluble fraction was recovered by centrifugation at 20.000 g for 10 min. The enzymes were purified on NiNTA column (Qiagen), stored at 4° C. and used within a week. To carry out the enzyme inhibition assays under linear conditions, the final point test system for kinase activity measurement was used. Kinase was added to reaction mixture in such a way as to obtain linear activity with respect to the concentration of enzyme and with respect to time. For determination of kinase inhibition the reaction mixture contained 1 mg/ml histone H1 (type III-S, Sigma) in the presence of 15 μM ATP, 0.05 μCi [γ-$^{33}$P]ATP and the tested compound in a final volume of 10 μl; all in reaction buffer (50 mM HEPES, 10 mM $MgCl_2$, 5 mM EGTA, 10 mM 2-glycerolphosphate, 1 mM NaF, 1 mM DTT, pH 7.4). After 20 min incubation, the reactions were stopped by the addition of 5 μl of a 3% $H_3PO_4$, aliquots were spotted on P-81 phosphocellulose (Whatman, USA) that was subsequently washed 3× with 5% $H_3PO_4$ and finally air dried. The measurements of kinase inhibition employed digital image analyzer BAS-1800 (Fujifilm, Japan). Kinase activity was usually expressed as a percentage of maximum activity. The compound concentration decreasing the CDK kinase activity to 50% was determined from dose-response curves and designated as $IC_{50}$. For the purpose of kinetic analysis, the activity was expressed as arbitrary units (AU) of digital image analyzer signal.

TABLE 3

Kinase inhibitory activity ($IC_{50}$ values given in μM) of selected 4-arylazo-3;5-diamino-pyrazole derivatives

| No. | $IC_{50}$ (μM)$^a$ CDK1 | CDK2 |
|---|---|---|
| 1b | 25 | 22 |
| 2b | 100 | 100 |
| 3b | 25 | 24 |
| 4b | 60 | 45 |
| 5b | >100 | 100 |
| 6b | >100 | 100 |
| 7b | 2.6 | 6.1 |
| 8b | 4.8 | 23 |
| 9b | 16 | 40 |
| 10b | 3.6 | 2.5 |
| 11b | 6.0 | 6 |
| 12b | 2.1 | 3.5 |
| 13b | 70 | 88 |
| 14b | 34 | 27 |
| 15b | 100 | 100 |

TABLE 3-continued

Kinase inhibitory activity (IC$_{50}$ values given in µM)
of selected 4-arylazo-3,5-diamino-pyrazole derivatives

| No. | IC$_{50}$ (µM)[a] | |
|---|---|---|
| | CDK1 | CDK2 |
| 16b | 21 | 17 |
| 17b | >100 | >100 |
| 18b | >100 | >100 |
| 19b | >100 | 100 |
| 20b | >100 | >100 |
| 21b | >100 | >100 |
| 22b | >100 | >100 |
| 23b | >100 | >100 |
| 24b | >100 | >100 |
| 25b | >100 | >100 |
| 26b | 100 | 95 |
| 27b | >100 | >100 |
| 28b | 5.5 | 10 |
| 29b | 16 | 15 |
| 30b | >100 | >100 |
| 31b | >100 | >100 |
| 32d | >100 | >100 |
| 33d | >100 | >100 |
| 34d | >100 | >100 |
| 35d | >100 | >100 |
| 36d | >100 | >100 |
| olomoucine | 6.5 | 5 |

[a] All values are averaged from triplicates.

Table 3 shows the results of inhibitory activity of novel compounds against CDK1 and CDK2 in comparison with the data on a prototype compound (trisubstituted purine olomoucine). Most of the 4-arylazo-3,5-diamino-pyrazole derivatives showed marked inhibitory activity in in vitro kinase assays.

Routine screening of compound library for protein kinase inhibitors yielded in the identification of 1 as the first representative of a novel substance group able to diminish the catalytic activity of CDK1 and 2. In the effort to reveal basic relationships between the structure and activity, a number of analogous derivatives were synthesized and evaluated. Due to the synthetic route used, the derivatives differed only in 4-arylazo moiety.

Studies revealed that 4-phenylazo substituted 3,5-diaminopyrazoles bearing an additional small polar group on the phenyl ring are particularly active (derivatives 7b-12b, 14b, 16b and others summarized in FIG. 1 and Table 3). The most effective from the series were hydroxy and nitro compounds, respectively. In the case of hydroxyphenyl derivatives, especially ortho substituted 10b and para substituted 12b gave the best IC$_{50}$ values, whereas meta-hydroxy derivative 11b was about half as effective on both CDK1 and 2. Further modification, i.e. insertion of a methylene group in between 2-OH and phenyl (16b), led to a decrease in activity, when compared to homologue 10b.

Interestingly, the nitrated compounds 7b-9b showed a different positional effect. Here, the position of NO$_2$ group affected CDK activity in order ortho>meta>para, with a 2-4 fold drop of inhibition between the respective isomers. Moreover, an increased selectivity on CDK1 over CDK2 was observed. 4-Halogenophenyl derivatives 3b-6b and non-polar 4-methylphenyl derivative 2b displayed decreased activity, although fluorinated compound 3b retained the same activity as 1b carrying the unsubstituted phenyl ring. Other non-polar substituents also retained the inhibitory activity on the level of 1b, for example bulky naphthalen-1-yl derivative 28b (but not isomeric 29b) or saturated 30b. These data indicate that larger side chains would also be acceptable for CDK1/2 inhibitors. However, when bulky arylamines were used as initial precursors, the resulting diaminopyrazoles 18b-27b did not displayed relevant CDK inhibitory activity. The explanation for this decrease could be due to occupation of the para position on phenyl ring, which seems to have a detrimental effect probably caused by a steric hindrance within hydrophobic pocket. This effect is probably also responsible for the low activity (almost zero) of p-aminomethyl derivative 17b.

The last subgroup of new derivatives was obtained from bisdiazonium salts and contained two relatively bulky 3,5-diamino-pyrazole cycles.

Example 3

Kinase Selectivity

In order to better characterize the pyrazole derivatives, the most active CDK inhibitor 12b was assayed with 10 other protein kinases at a fixed concentration of 10 µM. The panel included purified recombinant human protein kinases listed in Table 4 below. Most of the kinases tested were inhibited poorly or not at all, including another cyclin-dependent kinase family member CDK7, sharing a high similarity with CDK1 and 2, which is also usually sensitive to CDK1 inhibitors. Surprisingly, the compound showed disctinct selectivity profile when compared to other CDK inhibitors. For example, the trisubstituted purines (olomoucine, roscovitine) also have a strong effect on MAPK1 and CDK7 (Knockaert et al, Chem Biol. 2000 June; 7(6):411-22, Cohen 2003) and paullones and aloisines block GSK3β (Cohen 2003, Mettey et al, J Med Chem. 2003 Jan. 16; 46(2):222-36 2003). However, in the case of 4-phenylazo-3,5-diamino-pyrazole CDK1/2 inhibitors however the structurally different p70S6K was found to be sensitive to 12b with an IC$_{50}$ about 10 µM. Although p70S6 kinase belongs to the potential intracellular targets of purvalanol B as proved by affinity chromatography (Knockaert et al, 2000, ibid), the selectivity of this compound does not resemble any other pharmacological CDK inhibitor and the actual profile of its binding proteins within the cell remains to be verified.

TABLE 4

Selectivity of 12b for various protein kinases.

| Protein Kinase | % of kinase activity[a] |
|---|---|
| CDK1/cyclin B | 19 |
| CDK2/cyclin E | 31 |
| CDK7/cyclin H | 71 |
| c-Abl | 84 |
| CHK1 | 89 |
| CK2 | 65 |
| GSK3β | 81 |
| MAPK1 | 99 |
| p70S6K | 51 |
| PKA | 67 |
| PKBα | 105 |
| SAPK2α | 82 |

[a] % of kinase activity in the presence of 10 µM compound.

The increase of the inhibitory potency of hydroxyphenyl derivatives over the starting compound (unsubstituted phenyl) led to speculation that 4-phenylazo moiety may occupy the hydrophobic pocket, partially due to its homology with 6-benzylamino side chain of 2,6,9-trisubstituted purine CDK inhibitors. The SAR profile of three hydroxy derivatives, where the most active isomers 10b and 12b are substituted at either ortho or para position, also resembles that of purine inhibitors with the hydroxybenzylamino chains. Attempts were made to improve the inhibitor interaction with the CDK2 protein by preparing the derivative 21b analogous to oxoindole 91 with sulphonamide group at phenyl ring, that positively affects the binding (ref. Bramson 2001). However 21b failed to inhibit the enzyme as well as smaller acetyl derivative 18b, suggesting that the binding mode probably differs from that expected.

Example 4

In vitro Cytotoxic Activity of Novel Compounds

The following cell lines were used: HELA (human cervical carcinoma), MCF7 (human breast adenocarcinoma), NIH 3T3 (mouse fibroblasts), HOS (human osteogenic sarcoma), HL 60 (human promyelocytic leukemia), G 361 (human malignant melanoma), K562 (human chronic myeloblastic leukemia), CEM (human lymphoblastoid leukaemia). Tested drugs were added to the cell cultures in six different concentration and kept at 37° C. and 5% $CO_2$ for three days.

The cells, cultured in DMEM (supplemented with 10% fetal calf serum, 4 mM glutamine, 100 IU/ml penicillin, 100 µg/ml streptomycin) in a humidified $CO_2$ incubator at 37° C., were redistributed into 96-well microtitre plates (10.000 cells per well). After 12 h preincubation, tested compounds in six-fold dilutions were added. Treatment of cells with the tested compounds (in the 1-100 µM range) lasted for 72 h. At the end of this period, the cells were fed for 1 h with Calcein AM and the fluorescence of the live cells was measured at 485 nm/538 nm (ex/em) with a Fluoroskan Ascent (Labsystems, Finland). $IC_{50}$ values, the drug concentrations lethal to 50% of the tumor cells, were determined from the dose-response curves (FIG. 1).

The cytotoxicity of novel compounds was tested on panel of cell lines of different histogenetic and species origin (Table 5). Higher activities were found in all tumour cell lines tested. Notably, the higher effectiveness of novel derivatives was also found in cell lines bearing various mutations or deletions in cell cycle associated proteins, e.g. HL-60, BT549, Hela, U2OS, MDA-MB231, and Saos2. This indicates that these substances should be equally effective in tumours with various alterations of tumour suppressor genes, namely p53, Rb, etc. Importantly, this observation distinguishes the novel compounds from flavopiridol and related compounds, as their biological activity is dependent on p53 status.

All CDK inhibitors described so far show in vitro antiproliferative properties against a panel of cancer cell lines independent of their selectivity and potency. Therefore 10 of the most active 4-phenylazo-3,5-diamino-pyrazole CDK1/2 inhibitors were tested against four cell lines differing substantially in tumor origin. The results are summarized in Table 5. Except for the derivatives 8b, 9b, 12b, and 30b, all the compounds showed only marginal cytotoxicity, with $IC_{50}$ values over 100 µM. Such a low activity is comparable to that of olomoucine, a well known but weak inhibitor of CDK1 and 2, killing 50% of cell population at concentrations above 100 µM. In general, the derivatives substituted with bulky aryl moieties (e.g. sulfonamides 18b-23b or double azoderivatives 32d-35d) demonstrated lower antiproliferative activity, while some pyrazoles with smaller 4-aryl side chains displayed measurable $IC_{50}$ values.

Surprisingly, a positional effect of hydroxy and nitrophenyl substituents on the activity was observed, that did not simply reflect the CDK inhibitory pattern. The hydroxylated compounds 10b and 12b (the most potent CDK1/2 inhibitors), showed significant difference in a cell proliferation assay. Compound 12b caused expected cytotoxicity against all four cell lines used, but in contrast 10b and 11b, despite their potent CDK1/2 activity, triggered a much weaker effect. On the other hand, the nitroderivatives 7b and 9b, differing in CDK inhibition (app. 7-times), evoked in vitro anticancer activity at comparable concentrations.

Noteworthy, compound 30b, with only a weak impact on CDK activity, showed a cytotoxicity even exceeding olomoucine anticancer properties. Such dramatic changes in cytotoxicity of the new substance series is probably connected with changes of molecule polarity, that may facilitate penetration through membranes and also alter the enzyme binding. In summary, the discrepancies between kinase inhibition and cytotoxicity suggest, that some other cellular targets beyond CDK1 and 2 may be hit with the pyrazole compounds.

TABLE 5

Cytotoxicity of Novel Compounds for Different Cancer Cell Lines

| No. | R1 | $IC_{50}$ (µM) (or % of viable cells[a]) | | | |
|---|---|---|---|---|---|
| | | MCF7 | HOS | G361 | K562 |
| 1b | phenyl | >100 | >100 | >100 | >100 |
| | | (74 ± 5%) | (83 ± 8%) | (75 ± 2%) | (90 ± 14%) |
| 7b | 2-nitrophenyl | >100 | >100 | >100 | 100 ± 10 |
| | | (62 ± 9%) | (57 ± 6%) | (58 ± 2%) | (48 ± 4%) |
| 8b | 3-nitrophenyl | 65 ± 7 | >100 | >100 | 79 ± 6 |
| | | (44 ± 6%) | (95 ± 5%) | (69 ± 8%) | (28 ± 5%) |
| 9b | 4-nitrophenyl | >100 | >100 | >100 | 71 ± 6 |
| | | (60 ± 4%) | (80 ± 8%) | (61 ± 10%) | (25 ± 3%) |
| 10b | 2-hydroxyphenyl | >100 | >100 | >100 | >100 |
| | | (72 ± 6%) | (84 ± 7%) | (74 ± 12%) | (72 ± 8%) |
| 11b | 3-hydroxyphenyl | >100 | >100 | >100 | >100 |
| | | (71 ± 9%) | (83 ± 8%) | (70 ± 10%) | (53 ± 6%) |
| 12b | 4-hydroxyphenyl | 33 ± 5 | 49 ± 9 | 64 ± 5 | 62 ± 8 |
| | | (20 ± 6%) | (22 ± 8%) | (8.3 ± 4%) | (23 ± 7%) |
| 16b | 2-hydroxymethylphenyl | >100 | >100 | >100 | >100 |
| | | (51 ± 10%) | (87 ± 8%) | (84 ± 11%) | (86 ± 2%) |
| 28b | naphth-1-yl | >100 | >100 | >100 | 50 ± 3 |
| | | (56 ± 1%) | (79 ± 8%) | (55 ± 14%) | (7.7 ± 6%) |
| 30b | 5,6,7,8-tetrahydronaphth-1-yl | 81 ± 9 | 92 ± 5 | 77 ± 4 | 55 ± 1 |
| | | (39 ± 10%) | (32 ± 6%) | (27 ± 5%) | (26 ± 7%) |
| | olomoucine | 134 ± 5 | 144 ± 15 | 147 ± 5 | 145 ± 9 |

[a]% of viable cells at 100 µM. All values are averaged from triplicates.

Example 5

Molecular and Cellular Effects of New Derivatives

For direct immunoblotting, total cellular protein lysates were prepared by harvesting treated cells in Laemmli sample buffer. Proteins were separated on 10% SDS-polyacrylamide gel and transferred onto a nitrocellulose membrane. The blotted membranes were stained with Ponceau-S in 1% acetic acid to verify equal protein loading, destained and blocked in PBS and 0,1% Tween 20 (PBS-T) with 5% low fat milk. The probing with anti-PARP monoclonal antibody (clone C-2-10) diluted 1:1000 lasted for 2 h at 22° C. After washing three times in PBS-T, the membrane was incubated with a 1:1000 dilution of peroxidase conjugated rabbit antimouse immunoglobulin. After another three washes in PBS-T, peroxidase activity was detected by ECL chemiluminiscence reagents (Amersham) according to the manufacturer's instructions.

Figure 3:
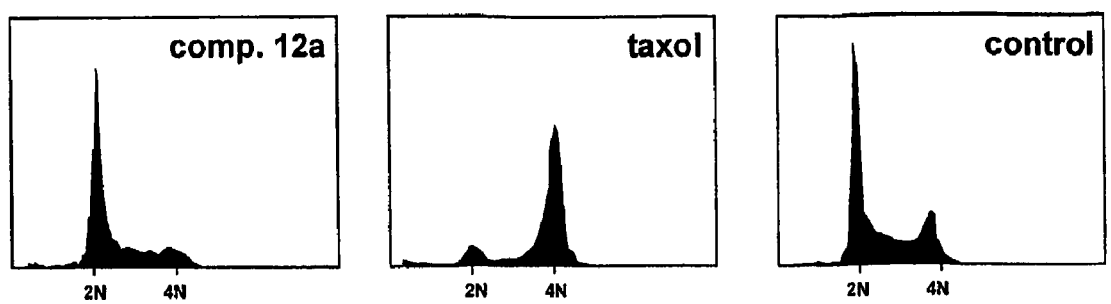
FIG. 3 shows cell cycle analysis of K562 cells treated with compound 12b (50 μM) for 24 h period. Taxol (1 μM) treated and control cells were harvested and analyzed simultaneously.

The antiproliferative activity of 4-arylazo-3,5-diaminopyrazoles was subsequently verified by flow cytometry with subconfluent and asynchronously growing K562 cell line. For the treatment of cells, compound 12b was selected because it showed both good anti-CDK and growth inhibitory activity. In accordance with the CDK1/cyclin B inhibition in vitro, the compound 12b caused accumulation of cell population in G1 already after 12 h incubation (FIG. 3). The cell cycle block in G2/M was not dominant. This result is however consistent with the ability of the compound to inhibit CDK1 as well as CDK2 to the same extent. Moreover, the compound 12b effect (at concentration used) leading to the G2/M cell cycle block equal to that of olomoucine, a similarly active CDK1/2 inhibitor used in previous experiments (Schutte B et al, Exp Cell Res. 1997 Oct. 10; 236(1):4-15).

Figure 4:
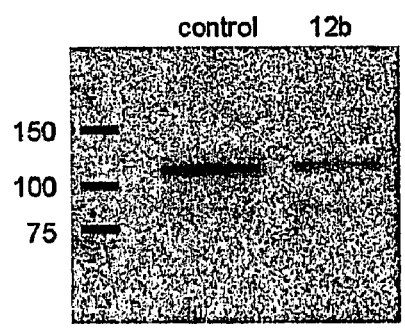
FIG. 4 shows fragmentation of PARP in MCF7 cells treated with compound 12b for 72 h.

After a longer incubation period (48-72 h) the cells started to die, with the some morphological features typical for apoptosis. Flow cytometry analysis revealed a sub-G1 peak of cell fragments, containing fragmented DNA (FIG. 3). The induction of apoptosis was therefore verified by the detection of a poly(ADP-ribose)polymerase (PARP) cleavage fragment. PARP is specifically cleaved as a result of activation of upstream proapoptotic caspases into 89 kDa and 27 kDa peptides. The western blot analysis of K562 cells treated with the compound 12b, with an antibody, that recognizes full length PARP as well as its cleavage fragment, revealed a 89 kDa peptide (FIG. 4). As judged by western blotting and flow cytometry, a significant cell death occurs after 72 h treatment with 12b.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

The invention claimed is:

1. A method for treating a cancer selected from the group consisting of cervical cancer, breast cancer, sarcoma, melanoma and leukemia, said method comprising administering to a subject in need thereof 3,5-diamino-4-(5,6,7,8-tetrahydronapthalene-1-yl)phenylazo-pyrazole, and a pharmaceutically acceptable salt thereof.

2. The method of claim 1, wherein the cancer is leukemia.

* * * * *